US012162915B2

(12) United States Patent
Barnes

(10) Patent No.: US 12,162,915 B2
(45) Date of Patent: *Dec. 10, 2024

(54) CELL PENETRATING PEPTIDES THAT INHIBIT IRF5 NUCLEAR LOCALIZATION

(71) Applicant: Rutgers, The State University of New Jersey, New Brunswick, NJ (US)

(72) Inventor: Betsy J. Barnes, Glenwood Landing, NY (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 18/220,940

(22) Filed: Jul. 12, 2023

(65) Prior Publication Data

US 2024/0043482 A1 Feb. 8, 2024

Related U.S. Application Data

(60) Continuation of application No. 17/472,760, filed on Sep. 13, 2021, now Pat. No. 11,746,133, which is a continuation of application No. 16/570,291, filed on Sep. 13, 2019, now Pat. No. 11,130,790, which is a division of application No. 15/758,276, filed as application No. PCT/US2016/051114 on Sep. 9, 2016, now abandoned.

(60) Provisional application No. 62/215,896, filed on Sep. 9, 2015.

(51) Int. Cl.
*C07K 14/00* (2006.01)
*A61K 38/00* (2006.01)
*A61P 37/02* (2006.01)
*C07K 14/47* (2006.01)

(52) U.S. Cl.
CPC .......... *C07K 14/4702* (2013.01); *A61P 37/02* (2018.01); *A61K 38/00* (2013.01); *C07K 2319/09* (2013.01); *C07K 2319/10* (2013.01)

(58) Field of Classification Search
CPC .... C07K 14/4702; C07K 14/47; C07K 14/00; C07K 2319/09; C07K 2319/10; A61P 37/02; A61K 38/00
See application file for complete search history.

(56) References Cited

U.S. PATENT DOCUMENTS

| 11,130,790 B2 | 9/2021 | Barnes |
| 2003/0224383 A1 | 12/2003 | West et al. |
| 2009/0082250 A1 | 3/2009 | Hart et al. |
| 2010/0158968 A1 | 6/2010 | Panitch et al. |
| 2014/0030218 A1 | 1/2014 | Udalova et al. |

FOREIGN PATENT DOCUMENTS

| DE | 10334777 A1 | 2/2005 |
| WO | 2014056813 A1 | 4/2014 |

OTHER PUBLICATIONS

Barnes, et al., "Multiple Regulatory Domains of IRF-5 Control Activation, Cellular Localization, and Induction of Chemokines That Mediate Recruitment of T Lymphocytes.", Mol Cell Biol 22(16), 5721-5740 (2002).
Bowdish, et al., "The Human Cationic Peptide LL-37 Induces Activation of the Extracellular Signal-Regulated Kinase and p38 Kinase Pathways in Primary Human Monocytes.", J Immunol 172, 3758-3765 (2004).
Chen, et al., "Insights into interferon regulatory factor activation from the crystal structure of dimeric IRF5.", Nat Struct Mol Biol 15(11), 1213-1220 (2008).
Cheng, et al., "Differential Activation of IFN Regulatory Factor (IRF)-3 and IRF-5 Transcription Factors during Viral Infection.", J Immunol 176, 7462-7470 (2006).
Feng, et al., "Genetic variants and disease-associated factors contribute to enhanced interferon regulatory factor 5 expression in blood cells of patients with systemic lupus erythematosus.", Arthritis Rheum 62(2), 562-573 (2010).
Feng, et al., "Protection of Irf5-deficient mice from pristane-induced lupus involves altered cytokine production and class switching.", Eur J Immunol 42(6), 1477-1487 (2012).
Foreman, et al., "Activation of Interferon Regulatory Factor 5 by Site Specific Phosphorylation.", PLoS ONE 7(3), e33098 (2012).
Hedl, et al., "IRF5 risk polymorphisms contribute to interindividual variance in pattern recognition receptor-mediated cytokine secretion in human monocyte-derived cells.", J Immunol 188(11), 5348-5356 (2012).
Mancl, et al., "Two Discrete Promoters Regulate the Alternatively Spliced Human Interferon Regulatory Factor-5 Isoforms", The Journal of Biological Chemistry, vol. 280, No. 22, p. 21078-21090 (2005).
Niewold, et al., "Association of the IRF5 Risk Haplotype With High Serum Interferon-α Activity in Systemic Lupus Erythematosus Patients.", Arthritis Rheum 58(8), 2481-2487 (2008).
Patent Cooperation Treaty, International Searching Authority, Search Report and Written Opinion for PCT/US2016/051114, 13 pages (Jun. 9, 2017).
Pimenta, et al., "A conserved region within interferon regulatory factor 5 controls breast cancer cell migration through a cytoplasmic and transcription-independent mechanism", Molecular Cancer, vol. 14, No. 32 p. 1-13 (2015).

(Continued)

*Primary Examiner* — Julie Ha
(74) *Attorney, Agent, or Firm* — Amster, Rothstein & Ebenstein LLP

(57) ABSTRACT

The invention provides inhibitors of interferon regulatory factor 5 (IRF5) nuclear localization and methods of using the inhibitors to treat autoimmune diseases such as systemic lupus erythematosus (SLE).

6 Claims, 14 Drawing Sheets
Specification includes a Sequence Listing.

(56) References Cited

OTHER PUBLICATIONS

Stone, et al., "IRF5 activation in monocytes of SLE patients is triggered by circulating autoantigens independent of type I IFN.", Arthritis Rheum 64(3), 788-798 (2012).
Stone, et al., "RNA-Seq for Enrichment and Analysis of IRF5 Transcript Expression in SLE.", PLoS ONE 8(1), e54487 (2013).
Xu, et al., "Interferon regulatory factor 5 and autoimmune lupus.", Expert Rev Mol Med 15, e6 (2013).
Yang, et al., "Monocytes from Irf5-/- mice have an intrinsic defect in their response to pristane-induced lupus‡.", J Immunol 189(7), 3741-3750 (2012).
Q13568 from UniProt, pp. 1-16, Integrated into UniProtKB/Swiss-Prot Nov. 1, 1997.
De S. et al., "Development and characterization of a cell-penetrant IRF5 inhibitor," Rutgers New Jersey Medical School, presented at the ICIS Meeting, Australia 2014, poster.
De S et al., "Development and characterization of cell-penetrant IRF5 inhibitors," presented at the ICIS Meeting, Australia 2014, Abstract.
De S et al., "Characterizing the role of IRF5 in human B cell development of function," presented at the ICIS Meeting, Australia 2014, Abstract.

FIGURES 1A-B
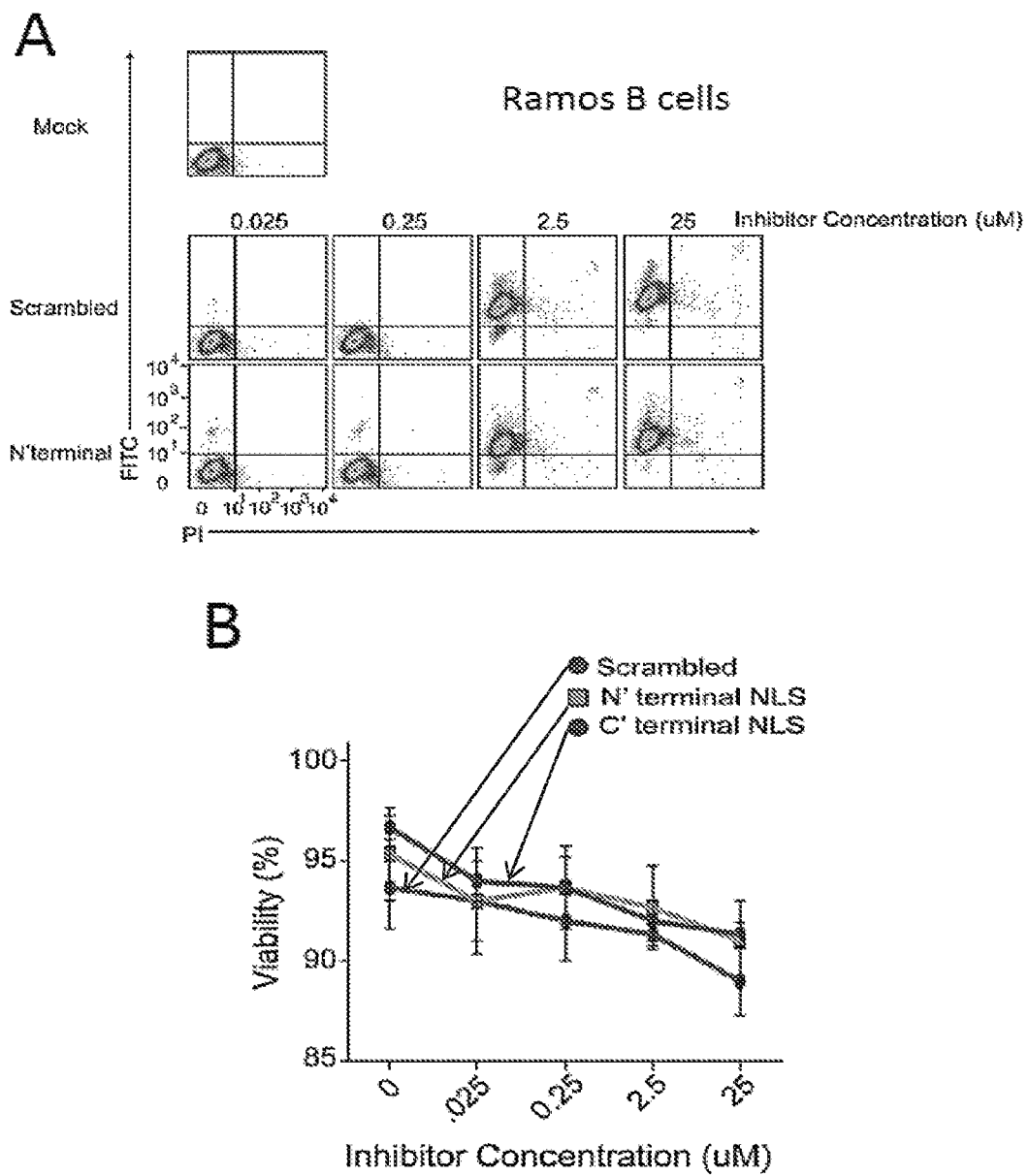

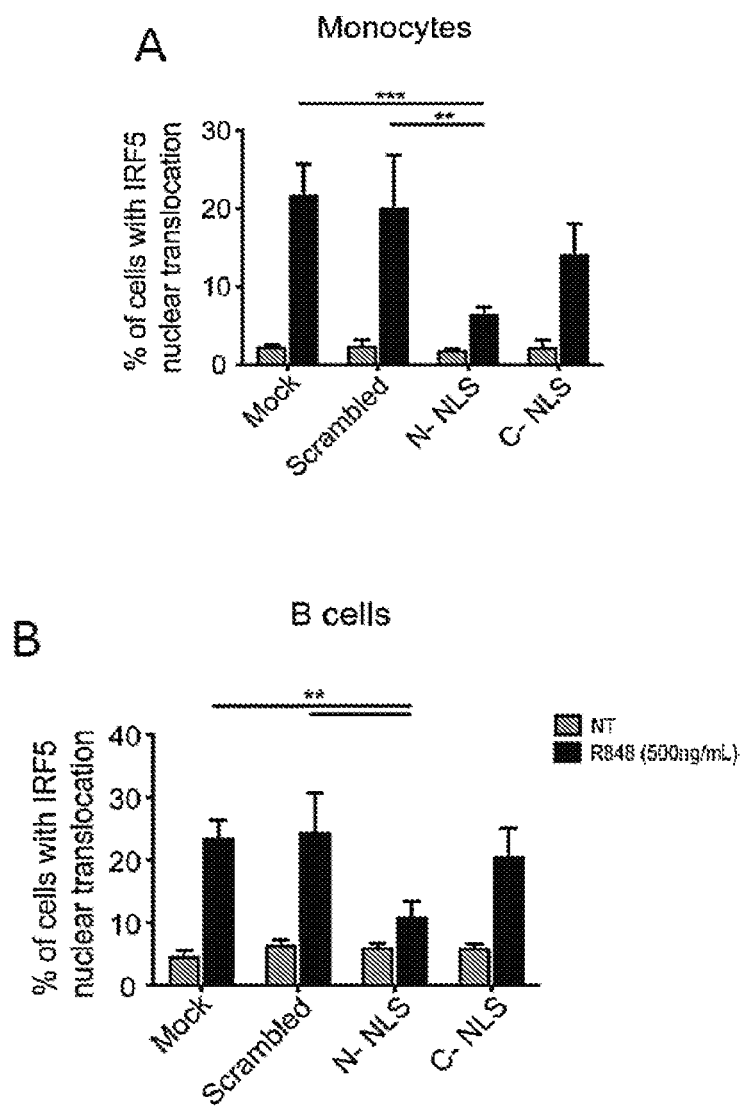
FIGURES 2A-B

FIGURES 2C-E
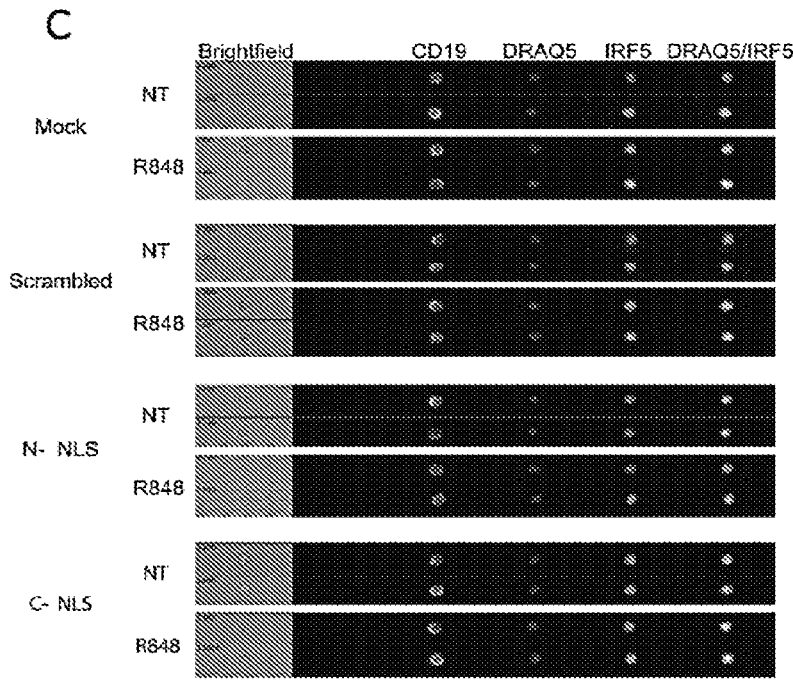
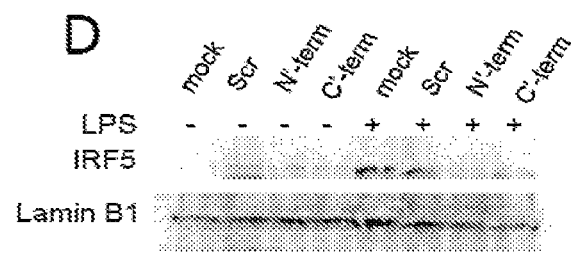
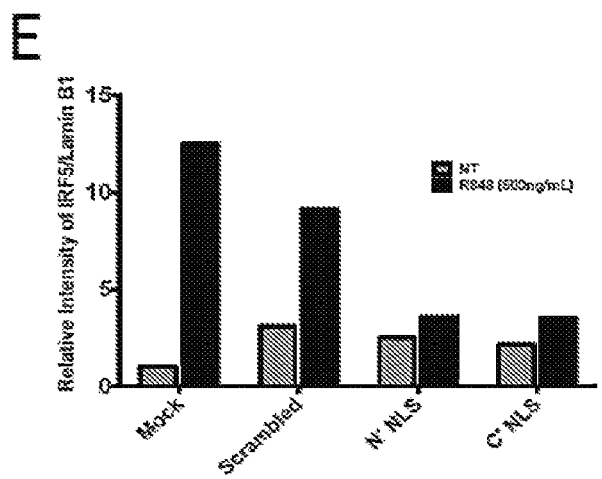

FIGURES 3A-B
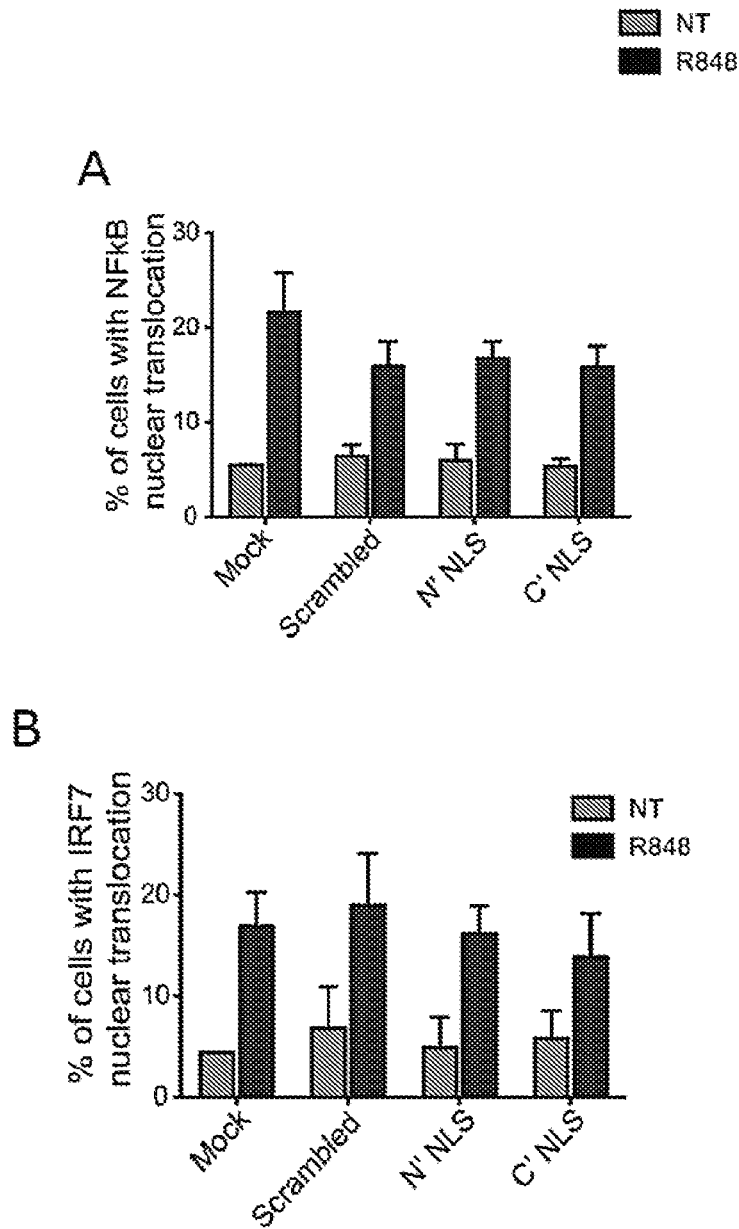

FIGURES 4A-C
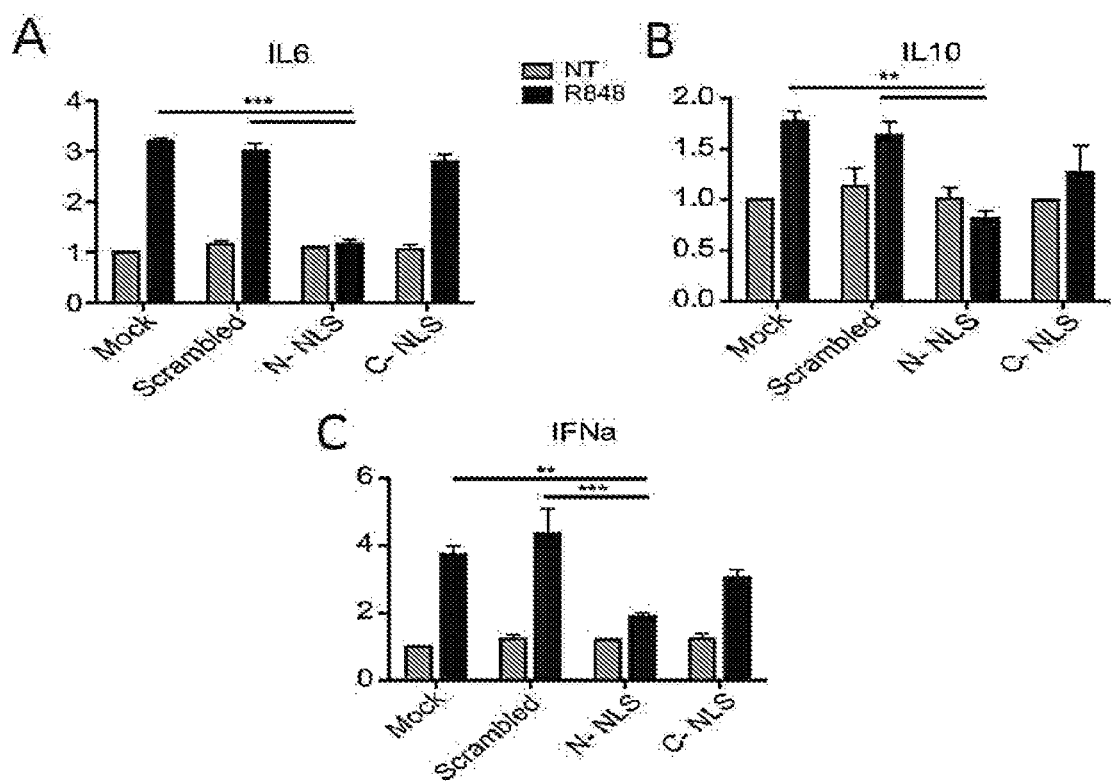

FIGURES 6A-B
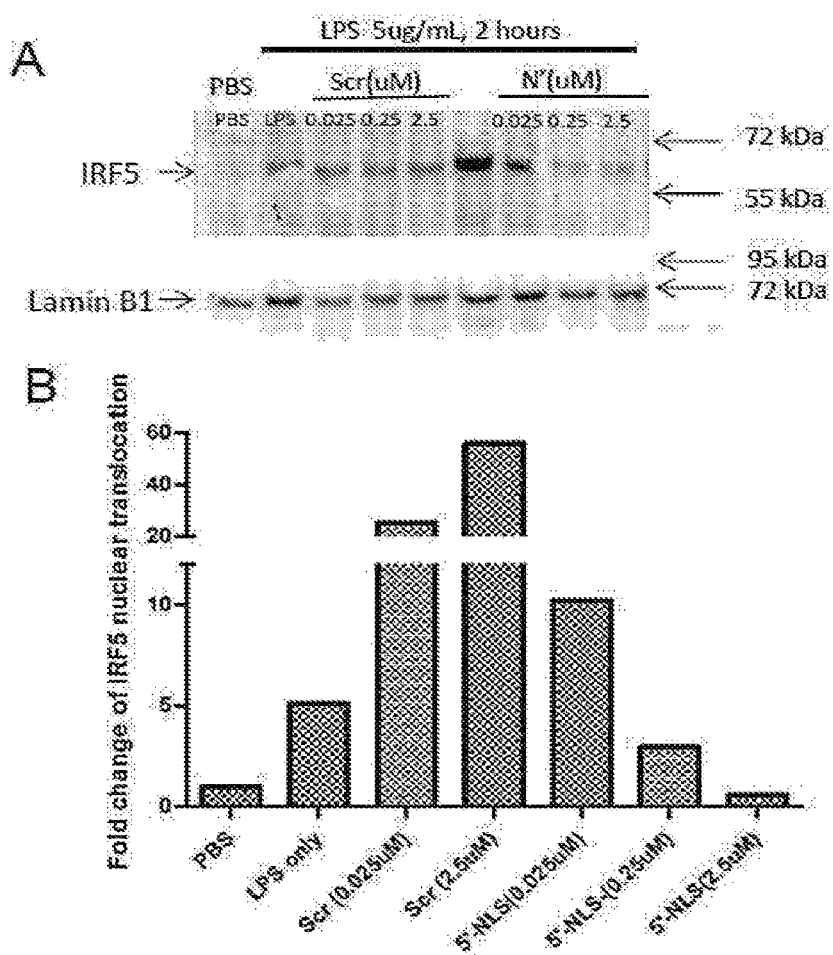

FIGURES 7A-B
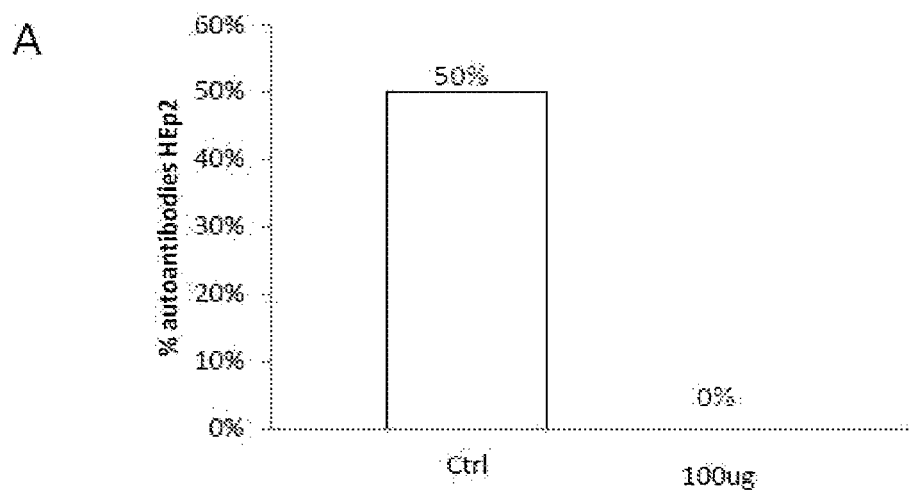
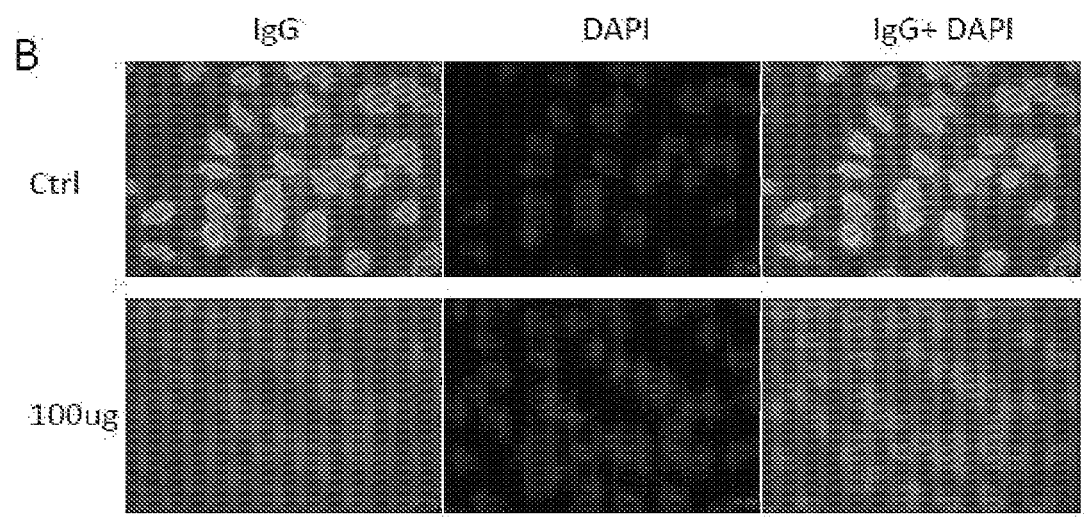

FIGURES 8A-B
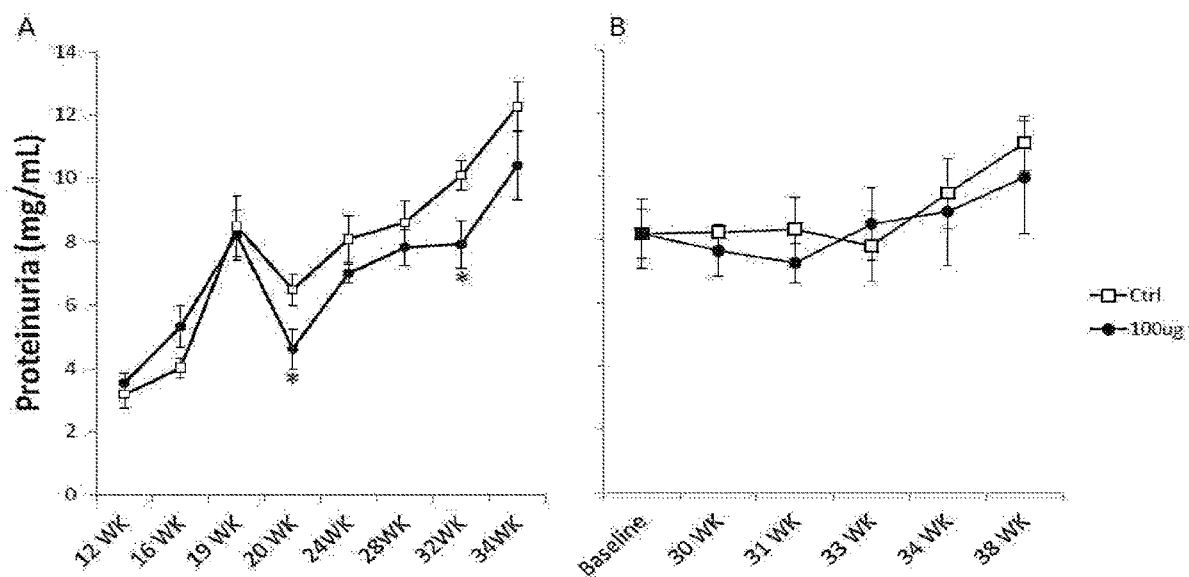

SEQUENCE LISTING

```
Sequence total quantity: 16
SEQ ID NO: 1            moltype = AA  length = 7
FEATURE                 Location/Qualifiers
REGION                  1..7
                        note = Synthetic peptide
source                  1..7
                        mol_type = protein
                        organism = synthetic construct
SEQUENCE: 1
PRRVRLK                                                                    7

SEQ ID NO: 2            moltype = AA  length = 7
FEATURE                 Location/Qualifiers
REGION                  1..7
                        note = Synthetic peptide
source                  1..7
                        mol_type = protein
                        organism = synthetic construct
SEQUENCE: 2
PREKKLI                                                                    7

SEQ ID NO: 3            moltype = AA  length = 24
FEATURE                 Location/Qualifiers
REGION                  1..24
                        note = Synthetic peptide
source                  1..24
                        mol_type = protein
                        organism = synthetic construct
SEQUENCE: 3
DRQIKIWFQN RRMKWKKPRR VRLK                                                24

SEQ ID NO: 4            moltype = AA  length = 24
FEATURE                 Location/Qualifiers
```

```
REGION                    1..24
                          note = Synthetic peptide
source                    1..24
                          mol_type = protein
                          organism = synthetic construct
SEQUENCE: 4
DRQIKIWFQN RRMKWKKPRE KKLI                                              24

SEQ ID NO: 5              moltype = AA  length = 17
FEATURE                   Location/Qualifiers
REGION                    1..17
                          note = Synthetic peptide
source                    1..17
                          mol_type = protein
                          organism = synthetic construct
SEQUENCE: 5
DRQIKIWFQN RRMKWKK                                                      17

SEQ ID NO: 6              moltype = AA  length = 24
FEATURE                   Location/Qualifiers
REGION                    1..24
                          note = Synthetic peptide
source                    1..24
                          mol_type = protein
                          organism = synthetic construct
SEQUENCE: 6
DRQIKIWFQN RRMKWKKPKR RRLV                                              24

SEQ ID NO: 7              moltype = AA  length = 24
FEATURE                   Location/Qualifiers
REGION                    1..24
                          note = Synthetic peptide
source                    1..24
                          mol_type = protein
                          organism = synthetic construct
SEQUENCE: 7
DRQIKIWFQN RRMKWKKPIK RLKE                                              24

SEQ ID NO: 8              moltype = AA  length = 7
FEATURE                   Location/Qualifiers
REGION                    1..7
                          note = Synthetic peptide
source                    1..7
                          mol_type = protein
                          organism = synthetic construct
SEQUENCE: 8
PKRRRLV                                                                  7

SEQ ID NO: 9              moltype = AA  length = 16
FEATURE                   Location/Qualifiers
REGION                    1..16
                          note = Synthetic peptide
source                    1..16
                          mol_type = protein
                          organism = synthetic construct
SEQUENCE: 9
AAVALLPAVL LALLAP                                                       16

SEQ ID NO: 10             moltype = AA  length = 13
FEATURE                   Location/Qualifiers
REGION                    1..13
                          note = Synthetic peptide
source                    1..13
                          mol_type = protein
                          organism = synthetic construct
SEQUENCE: 10
GRKKRRQRRR PPQ                                                          13

SEQ ID NO: 11             moltype = AA  length = 17
FEATURE                   Location/Qualifiers
REGION                    1..17
                          note = Synthetic peptide
source                    1..17
                          mol_type = protein
                          organism = synthetic construct
SEQUENCE: 11
CSIPPEVKFN KPFVYLI                                                      17

SEQ ID NO: 12             moltype = AA  length = 17
```

```
FEATURE                 Location/Qualifiers
REGION                  1..17
                        note = Synthetic peptide
source                  1..17
                        mol_type = protein
                        organism = synthetic construct
SEQUENCE: 12
KKWKMRRNQF WVKVQRG                                                      17

SEQ ID NO: 13           moltype = AA  length = 18
FEATURE                 Location/Qualifiers
REGION                  1..18
                        note = Synthetic peptide
source                  1..18
                        mol_type = protein
                        organism = synthetic construct
SEQUENCE: 13
KLLKLLLKLW LKLLKLLL                                                     18

SEQ ID NO: 14           moltype = AA  length = 14
FEATURE                 Location/Qualifiers
REGION                  1..14
                        note = Synthetic peptide
source                  1..14
                        mol_type = protein
                        organism = synthetic construct
SEQUENCE: 14
INLKALAALA KKIL                                                         14

SEQ ID NO: 15           moltype = AA  length = 18
FEATURE                 Location/Qualifiers
REGION                  1..18
                        note = Synthetic peptide
source                  1..18
                        mol_type = protein
                        organism = synthetic construct
SEQUENCE: 15
RQIKIWFQNR RMKWKKGG                                                     18

SEQ ID NO: 16           moltype = AA  length = 27
FEATURE                 Location/Qualifiers
REGION                  1..27
                        note = Synthetic peptide
source                  1..27
                        mol_type = protein
                        organism = synthetic construct
SEQUENCE: 16
GWTLNSAGYL LGKINLKALA ALAKKIL                                           27
```

CELL PENETRATING PEPTIDES THAT INHIBIT IRF5 NUCLEAR LOCALIZATION

CROSS-REFERENCE TO RELATED APPLICATIONS

This application is a continuation of U.S. patent application Ser. No. 17/472,760, now U.S. Pat. No. 11,746,133, issued on Sep. 5, 2023, filed on Sep. 13, 2021, which is a continuation of U.S. patent application Ser. No. 16/570,291, filed on Sep. 13, 2019, now U.S. Pat. No. 11,130,790, issued on Sep. 28, 2021, which is a divisional of U.S. patent application Ser. No. 15/758,276, filed on Mar. 7, 2018, now abandoned, which is a U.S. national stage entry under 35 U.S.C. § 371 of PCT International Patent Application No. PCT/US2016/051114, filed on Sep. 9, 2016, which claims the benefit of U.S. Provisional Application Ser. No. 62/215,896, filed on Sep. 9, 2015, the contents of which are incorporated herein by reference in their entirety.

INCORPORATION BY REFERENCE OF SEQUENCE LISTING XML

The Sequence Listing entitled "220,949.xml", created on Sep. 29, 2023, 26 KB, submitted electronically using the Patent Center is incorporated by reference as the Sequence Listing XML for the subject application.

BACKGROUND

Systemic lupus erythematosus (SLE) is an autoimmune disease in which the body's immune system mistakenly attacks healthy tissue. The underlying cause of SLE is not known. SLE symptoms vary from person to person and generally include joint pain and swelling, with some patients developing arthritis. Unfortunately, there is no cure for SLE, and the goal of treatment is to control symptoms. Further, side effects from certain treatments can be severe. As such, new tools for investigating SLE and treatments for SLE are needed.

SUMMARY OF THE INVENTION

Certain embodiments of the invention provide a polypeptide that comprises a cell penetrating peptide sequence and an interferon regulatory factor 5 (IRF5) nuclear localization signal (NLS) sequence. In certain embodiments, the polypeptide comprises formula (I):

X—Y—Z  (I)

wherein X is a cell penetrating peptide sequence; Y is a linking group; and Z an IRF5 NLS sequence.

As used herein, the term "cell penetrating peptide sequence" refers to any amino acid sequence that facilitates cellular intake/uptake of the polypeptide. Cell penetrating peptide sequences typically have an amino acid composition that either contains a high relative abundance of positively charged amino acids such as lysine or arginine or has sequences that contain an alternating pattern of polar/charged amino acids and non-polar, hydrophobic amino acids. These two types of structures may be referred to as polycationic or amphipathic, respectively. A third class of cell penetrating peptide sequences are hydrophobic peptides, which contain only apolar residues, with low net charge or have hydrophobic amino acid groups that are important for cellular uptake. Cell penetrating peptide sequences are known in the art, and include, but are not limited to, e.g., DRQIKIWFQNRRMKWKK (SEQ ID NO:5), AAVALLPAVLLALLAP (SEQ ID NO:9), GRKKRRQRRRPPQ (SEQ ID NO: 10) (i.e., the HIV TAT sequence), CSIPPEVKFNKPFVYLI (SEQ ID NO:11), KKWKMRRNQFWVKVQRG (SEQ ID NO:12), KLLKLLLKLWLKLLKLLL (SEQ ID NO:13), INLKALAALAKKIL (SEQ ID NO:14), RQIKIWFQNRRMKWKKGG (SEQ ID NO:15) and GWTLNSAGYLLGKINLKALAALAKKIL (SEQ ID NO:16). In certain embodiments, these cell penetrating peptide sequences may be in the acid form. In certain embodiments, these cell penetrating peptide sequences may be in the amide form. Accordingly, in certain embodiments, the cell penetrating peptide sequence comprises a sequence at least 90%, 91%, 92%, 93%, 94%, 95%, 96%, 97%, 98%, 99% or 100% identical to DRQIKIWFQNRRMKWKK (SEQ ID NO:5), AAVALLPAVLLALLAP (SEQ ID NO:9), GRKKRRQRRRPPQ (SEQ ID NO:10), CSIPPEVKFNKPFVYLI (SEQ ID NO:11), KKWKMRRNQFWVKVQRG (SEQ ID NO:12), KLLKLLLKLWLKLLKLLL (SEQ ID NO:13), INLKALAALAKKIL (SEQ ID NO:14), RQIKIWFQNRRMKWKKGG (SEQ ID NO:15) or GWTLNSAGYLLGKINLKALAALAKKIL (SEQ ID NO:16). In certain embodiments, the cell penetrating peptide sequence comprises DRQIKIWFQNRRMKWKK (SEQ ID NO:5), AAVALLPAVLLALLAP (SEQ ID NO:9), GRKKRRQRRRPPQ (SEQ ID NO:10), CSIPPEVKFNKPFVYLI (SEQ ID NO:11), KKWKMRRNQFWVKVQRG (SEQ ID NO:12), KLLKLLLKLWLKLLKLLL (SEQ ID NO:13), INLKALAALAKKIL (SEQ ID NO:14), RQIKIWFQNRRMKWKKGG (SEQ ID NO: 15) or GWTLNSAGYLLGKINLKALAALAKKIL (SEQ ID NO:16). In certain embodiments, the cell penetrating peptide sequence is DRQIKIWFQNRRMKWKK (SEQ ID NO:5), AAVALLPAVLLALLAP (SEQ ID NO:9), GRKKRRQRRRPPQ (SEQ ID NO:10), CSIPPEVKFNKPFVYLI (SEQ ID NO:11), KKWKMRRNQFWVKVQRG (SEQ ID NO:12), KLLKLLLKLWLKLLKLLL (SEQ ID NO:13), INLKALAALAKKIL (SEQ ID NO:14), RQIKIWFQNRRMKWKKGG (SEQ ID NO:15) or GWTLNSAGYLLGKINLKALAALAKKIL (SEQ ID NO:16). In certain embodiments, the cell penetrating peptide sequence is DRQIKIWFQNRRMKWKK (SEQ ID NO:5).

As used herein, the term "interferon regulatory factor 5 (IRF5) nuclear localization signal (NLS) sequence" refers any sequence that can mimic IRF5 nuclear translocation signals. Two functional nuclear localization signals (NLS) have been identified and characterized in the IRF5 protein that are not conserved or homologous with NLSs in other IRFs. One NLS resides in the amino-terminus (PRRVRLK) (SEQ ID NO:1) and the other in the carboxyl-terminus (PREKKLI) (SEQ ID NO:2) (Barnes et al. (2002) *Mol Cell Biol* 22, 5721-5740). Accordingly, in certain embodiments, the IRF5 NLS sequence comprises a sequence at least 90%, 91%, 92%, 93%, 94%, 95%, 96%, 97%, 98%, 99% or 100% identical to PRRVRLK (SEQ ID NO:1) or PREKKLI (SEQ ID NO:2). In certain embodiments, the IRF5 NLS sequence comprises PRRVRLK (SEQ ID NO:1) or PREKKLI (SEQ ID NO:2). In certain embodiments, the IRF5 NLS sequence is PRRVRLK (SEQ ID NO:1) or PREKKLI (SEQ ID NO:2). In certain embodiments, the IRF5 NLS sequence is PRRVRLK (SEQ ID NO:1). In certain embodiments, the IRF5 NLS sequence is PREKKLI (SEQ ID NO:2).

The nature of the linking group (Y) is not critical, and may be any group that can link the cell penetrating peptide sequence to the IRF5 NLS sequence using known chemistry, provided that the linking group does not interfere with the activity of the cell penetrating peptide sequence or the IRF5 NLS sequence (i.e., its ability to inhibit endogenous IRF5 nuclear localization). For example, in certain embodiments, the linking group may be a bond, such as an amide bond (i.e., a traditional peptide bond). Other linking groups include, e.g., ketomethylene (e.g., —C(=O)—CH2- for —C(=O)—NH—), aminomethylene (CH2-NH), ethylene, olefin (CH=CH), ether (CH2-0), thioether (CH2-S), tetrazole, thiazole, retroamide, thioamide, or ester (see, e.g., Spatola (1983) in Chemistry and Biochemistry of Amino Acids, Peptides and Proteins, Vol. 7, pp. 267-357, "Peptide Backbone Modifications," Marcel Dekker, N.Y., incorporated herein by reference). In other embodiments, the linking group may comprise one or more amino acids.

Certain embodiments of the present invention provide a polypeptide that comprises a sequence at least 90% identical to DRQIKIWFQNRRMKWKKPRRVRLK (SEQ ID NO:3), DRQIKIWFQNRRMKWKKPREKKLI (SEQ ID NO:4), DRQIKIWFQNRRMKWKKPKRRRLV (SEQ ID NO:6) or DRQIKIWFQNRRMKWKKPIKRLKE (SEQ ID NO:7). In certain embodiments, the polypeptide comprises a sequence at least 90% identical to DRQIKIWFQNRRMKWKKPRRVRLK (SEQ ID NO:3) or DRQIKIWFQNRRMKWKKPREKKLI (SEQ ID NO:4).

Certain embodiments of the present invention provide a polypeptide that is substantially identical to DRQIKIWFQNRRMKWKKPRRVRLK (SEQ ID NO:3), DRQIKIWFQNRRMKWKKPREKKLI (SEQ ID NO:4), DRQIKIWFQNRRMKWKKPKRRRLV (SEQ ID NO:6) or DRQIKIWFQNRRMKWKKPIKRLKE (SEQ ID NO:7). In certain embodiments, the polypeptide is substantially identical to DRQIKIWFQNRRMKWKKPRRVRLK (SEQ ID NO:3) or DRQIKIWFQNRRMKWKKPREKKLI (SEQ ID NO:4).

In certain embodiments, the polypeptide comprises a sequence at least about 90, 91, 92, 93, 94, 95, 96, 97, 98, 99 or 100% identical to SEQ ID NO:3, SEQ ID NO:4, SEQ ID NO:6 or SEQ ID NO:7.

In certain embodiments, the polypeptide comprises a sequence at least 95% identical to SEQ ID NO:3, SEQ ID NO:4, SEQ ID NO:6 or SEQ ID NO:7. In certain embodiments, the polypeptide comprises a sequence at least 95% identical to SEQ ID NO:3 or SEQ ID NO:4.

In certain embodiments, the polypeptide comprises a sequence at least 99% identical to SEQ ID NO:3, SEQ ID NO:4, SEQ ID NO:6 or SEQ ID NO:7. In certain embodiments, the polypeptide comprises a sequence at least 99% identical to SEQ ID NO:3 or SEQ ID NO:4.

In certain embodiments, the polypeptide comprises SEQ ID NO:3, SEQ ID NO:4, SEQ ID NO:6 or SEQ ID NO:7. In certain embodiments, the polypeptide comprises SEQ ID NO:3 or SEQ ID NO:4. In certain embodiments, the polypeptide comprises SEQ ID NO:3. In certain embodiments, the polypeptide comprises SEQ ID NO:4.

Certain embodiments of the present invention provide the polypeptide DRQIKIWFQNRRMKWKKPRRVRLK (SEQ ID NO:3).

Certain embodiments of the present invention provide the polypeptide DRQIKIWFQNRRMKWKKPREKKLI (SEQ ID NO:4).

Certain embodiments of the present invention provide the polypeptide DRQIKIWFQNRRMKWKKPKRRRLV (SEQ ID NO:6).

Certain embodiments of the present invention provide the polypeptide DRQIKIWFQNRRMKWKKPIKRLKE (SEQ ID NO:7).

In certain embodiments, the polypeptide is an inhibitor of interferon regulatory factor 5 (IRF5).

In certain embodiments, the polypeptide is an inhibitor of interferon regulatory factor 5 (IRF5) nuclear localization.

Certain embodiments of the present invention provide a nucleic acid sequence encoding a polypeptide as described herein.

Certain embodiments of the present invention provide a pharmaceutical composition that comprises a polypeptide as described herein and a pharmaceutically acceptable carrier.

Certain embodiments of the present invention provide a method of inhibiting interferon regulatory factor 5 (IRF5) in an animal (e.g., a mammal, such as a patient) in need thereof, comprising administering to the patient a therapeutically effective amount of a polypeptide as described herein.

Certain embodiments of the present invention provide a method of inhibiting interferon regulatory factor 5 (IRF5) nuclear localization in an animal (e.g., a mammal, such as a patient) in need thereof, comprising administering to the patient a therapeutically effective amount of a polypeptide as described herein.

Certain embodiments of the present invention provide a method for treating, e.g., an autoimmune disease, in an animal (e.g., a mammal, such as a patient) in need of such treatment, comprising administering to the patient a therapeutically effective amount of a polypeptide as described herein.

In another aspect, the present invention provides methods for treating and/or ameliorating one or more symptoms associated an autoimmune disease in an animal (e.g., a mammal, such as a patient) in need of such treatment, wherein the methods each include the step of administering to the human a therapeutically effective amount of a polypeptide as described herein.

In certain embodiments, the autoimmune disease is systemic lupus erythematosus (SLE), systemic sclerosis (scleroderma), polymyositis/dermatomyositis, Crohn's disease, rheumatoid arthritis, periodontitis, SLE-associated atherosclerosis, Sjögren's syndrome, autoimmune encephalomyelitis, sarcoidosis, Behçet's disease, myasthenia gravis, lupus nephritis, inflammatory bowel disease, ankylosing spondylitis, primary biliary cirrhosis, colitis, juvenile idiopathic arthritis, pulmonary fibrosis, antiphospholipid syndrome, or psoriasis.

In certain embodiments, the autoimmune disease is systemic lupus erythematosus (SLE).

Certain embodiments of the present invention provide a method for treating an animal (e.g., a mammal, such as a patient) having classical Hodgkin lymphoma, atherosclerosis, cardiovascular disease, neuropathic pain, or certain amenable types of leukemia and lymphoma, such as T cell large granular lymphocyte leukemia, comprising administering to the patient a therapeutically effective amount of a polypeptide as described herein.

Certain embodiments of the present invention provide a polypeptide as described herein for use in medical treatment or diagnosis.

Certain embodiments of the present invention provide the use of a polypeptide as described herein to prepare a medicament useful for inhibiting interferon regulatory factor 5 (IRF5) in an animal (e.g., a mammal, such as a patient).

Certain embodiments of the present invention provide the use of a polypeptide as described herein to prepare a medicament useful for treating an autoimmune disease in an animal (e.g., a mammal, such as a patient).

Certain embodiments of the present invention provide the use of a polypeptide as described herein to prepare a medicament useful for treating classical Hodgkin lymphoma, atherosclerosis, cardiovascular disease, neuropathic pain, or certain amenable types of leukemia and lymphoma, such as T cell large granular lymphocyte leukemia in an animal (e.g., a mammal, such as a patient).

Certain embodiments of the present invention provide a polypeptide as described herein for use in therapy.

Certain embodiments of the present invention provide a polypeptide as described herein for the inhibiting interferon regulatory factor 5 (IRF5).

Certain embodiments of the present invention provide a polypeptide as described herein for the prophylactic or therapeutic treatment of an autoimmune disease.

Certain embodiments of the present invention provide a polypeptide as described herein for the prophylactic or therapeutic treatment of classical Hodgkin lymphoma, atherosclerosis, cardiovascular disease, neuropathic pain, or certain amenable types of leukemia and lymphoma, such as T cell large granular lymphocyte leukemia.

Certain embodiments of the present invention provide a polypeptide as described herein for use in treating classical Hodgkin lymphoma, atherosclerosis, cardiovascular disease, neuropathic pain, or certain amenable types of leukemia and lymphoma, such as T cell large granular lymphocyte leukemia.

Certain embodiments of the present invention provide a pharmaceutical composition for use in the treatment of an autoimmune disease, comprising a polypeptide described herein and a pharmaceutically acceptable carrier.

Certain embodiments of the present invention provide a pharmaceutical composition for use in the treatment of treating classical Hodgkin lymphoma, atherosclerosis, cardiovascular disease, neuropathic pain, or certain amenable types of leukemia and lymphoma, such as T cell large granular lymphocyte leukemia, comprising a polypeptide described herein and a pharmaceutically acceptable carrier.

Certain embodiments of the present invention provide the use of a polypeptide as described herein as a research tool, e.g., for studying interferon regulatory factor 5 (IRF5).

In certain embodiments of the present invention provides the use of a polypeptide as described herein for studying interferon regulatory factor 5 (IRF5) nuclear localization.

Certain embodiments of the present invention provide a kit comprising a polypeptide as described herein, at least one other therapeutic agent, and instructions for administering the polypeptide and the other therapeutic agent(s) to an animal to treat an autoimmune disease, classical Hodgkin lymphoma, atherosclerosis, cardiovascular disease, neuropathic pain, or certain amenable types of leukemia and lymphoma, such as T cell large granular lymphocyte leukemia.

BRIEF DESCRIPTION OF THE FIGURES

FIGS. 1A-E. IRF5 peptide inhibitors are cell permeable. FITC-conjugated inhibitor titrations for cell penetrance were performed by flow cytometry analysis (FIG. 1A). Cells were co-stained with propidium iodide to examine viability. Inhibitors have no significant effect on cell viability (FIG. 1B) or cell cycle (FIG. 1C) in Ramos B cells. FIG. 1D shows representative images from imaging flow cytometry of intracellular FITC-conjugated inhibitors in CD19+ B cells and CD14+ monocytes from healthy donors. Peripheral blood mononuclear cells (PBMCs) were pre-incubated with inhibitors for 1 hour before surface staining and permeabilization. Nuclei were stained with DRAQ5. FIG. 1E shows representative histogram plots of FITC-conjugated inhibitor staining in CD14+ monocytes and CD19+ B cells using flow cytometry.

FIGS. 2A-E. Peptides (non-FITC-conjugated) inhibit R848-induced IRF5 nuclear translocation. Healthy donor PBMCs were pre-incubated with peptide inhibitors for 1 hour and then stimulated for 2 hours with the Toll-like receptor agonist R848. IRF5 cellular localization was determined in CD14+ monocytes (FIG. 2A) and CD19+ B cells (FIG. 2B) by staining with intracellular IRF5 and DRAQ5. Similarity scores between IRF5 and DRAQ5 were determined on the Amnis Imagestream using IDEAS software. FIG. 2C shows representative images from FIG. 2B. FIG. 2D shows a representative Western blot of nuclear-localized IRF5 using nuclear extracts from purified CD14+ healthy donor monocytes. Lamin B1 serves as a nuclear protein loading control. Cells were pre-incubated with the indicated inhibitors for 1 hour and then stimulated with LPS for 2 hours. FIG. 2E shows results from densitometry analysis of nuclear IRF5 in FIG. 2D. IRF5 band intensity was normalized by Lamin B1, and relative fold change of IRF5 in nuclear portion was calculated over PBS treated sample. In FIGS. 2A-B and E, the bar on the left is mock (NT) and the bar on the right is R848.

FIGS. 3A-B. Peptide inhibitors are specific for IRF5. Human healthy donor PBMCs were pre-incubated with the indicated inhibitors for 1 hour and cells stimulated with R848 for 30 min (FIG. 3A) or 2 hours (FIG. 3B). NFκB nuclear translocation was determined in CD14+ monocytes (FIG. 3A) and IRF7 nuclear translocation in BDCA2+ CD123+ plasmacytoid dendritic cells by imaging flow cytometry.

FIGS. 4A-C. IRF5 peptide inhibitors inhibit R848-induced proinflammatory cytokine expression in PBMCs. The expression of IL6 (FIG. 4A), IL10 (FIG. 4B), and IFNA (FIG. 4C) was determined by quantitative real-time PCR after 6 hours stimulation of PBMCs with R848.

FIGS. 6A-B. Inhibition of nuclear translocation of murine IRF5 by IRF5 peptide inhibitor (N'terminal) in response to LPS stimulation. (FIG. 6A) RAW264.6 cells were treated with PBS or 5 μg/mL LPS for 2 hours. Scramble (Scr) or N'terminal were pre-incubated at the indicated concentrations for 1 hour before stimulation with LPS. Nuclear extracts were subjected to Western blotting with anti-IRF5 and anti-Lamin B1 antibodies. (FIG. 6B) IRF5 band intensity was normalized to Lamin B1, and relative fold change of IRF5 in nuclear portion was calculated over PBS treated sample.

FIGS. 7A-B. IRF5 N'terminal inhibitor protects NZB/W F1 from in vivo pathogenic autoantibody production. 8 week-old NZB/W mice were mock-injected or IP-injected over 2 weeks with 100 μg IRF5 peptide inhibitor. Autoantibodies were analyzed by testing sera (1:100 dilution) on HEp-2 cells from age-matched mock or treated NZB/W mice (FIG. 7A). Three out of six mice in control group (Ctrl) were positive and zero out of six in 100 μg-treated group (100 µg) were positive at week 27. Representative pictures from control and treated group were taken at the same exposure time (FIG. 7B).

FIGS. 8A-B. IRF5 peptide inhibitor reduces proteinuria in NZB/W mice. Proteinuria was measured by Bradford protein assay. NZB/W F1 mice were IP-injected with 100 µg/day N'terminal (100 µg) or 100 µl PBS (Ctrl, □) at 8-weeks of age (early onset) (FIG. 8A) or 27-weeks of age (late onset) (FIG. 8B), on day 0, 1, 4, 7 and 14. * p<0.05 vs Ctrl; n=6/group.

DETAILED DESCRIPTION

Systemic Lupus Erythematosus (SLE)

Figure 1C:
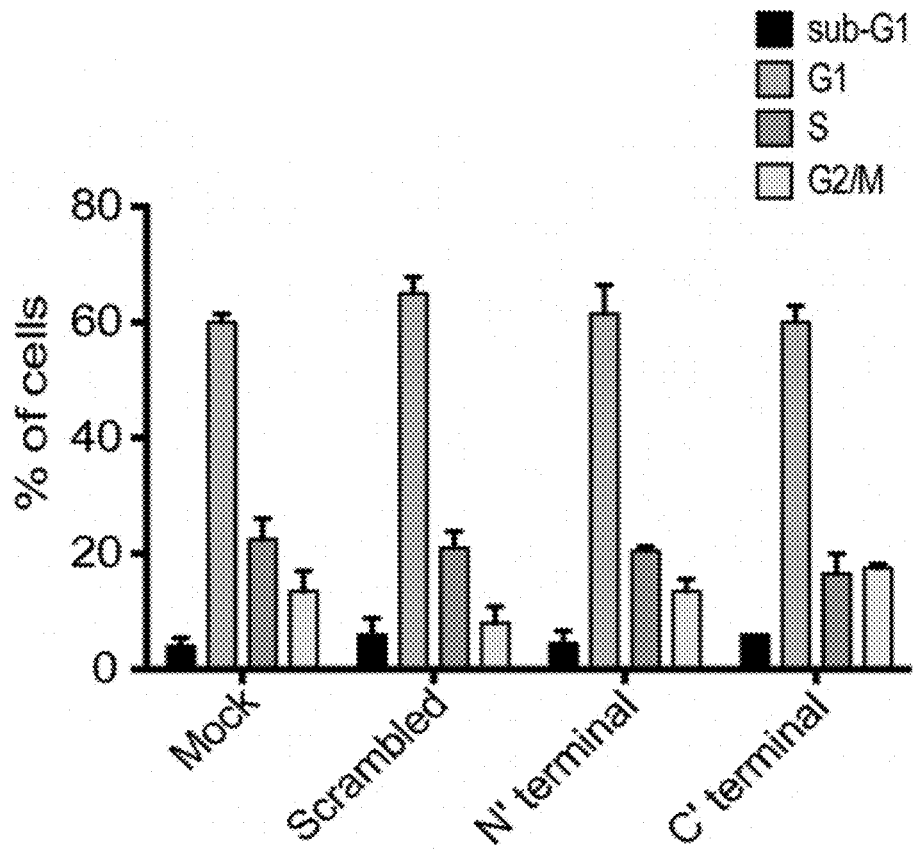

Systemic lupus erythematosus (SLE) is an autoimmune disease in which the body's immune system mistakenly attacks healthy tissue. SLE is more common in women than men. SLE may occur at any age but appears most often in people between the ages of 10 and 50. African Americans and Asians are affected more often than people from other races. SLE can affect the skin, joints, kidneys, brain, and other organs. The underlying cause of SLE is not fully understood. Symptoms vary from person to person, and may come and go. Almost everyone with SLE has joint pain and swelling, and some develop arthritis. The joints of the fingers, hands, wrists, and knees are often affected. Other common symptoms include: chest pain when taking a deep breath, fatigue, fever with no other cause, general discomfort, uneasiness, or ill feeling (malaise), hair loss, mouth sores, sensitivity to sunlight, skin rash (a "butterfly" rash occurs in about half people with SLE. The rash is most often seen over the cheeks and bridge of the nose, but can be widespread. It typically gets worse in sunlight), and swollen lymph nodes. Other symptoms depend on which part of the body is affected: brain and nervous system; headaches, numbness, tingling, seizures, vision problems, personality changes; digestive tract: abdominal pain, nausea, and vomiting; heart: abnormal heart rhythms (arrhythmias); lung: coughing up blood and difficulty breathing; skin: patchy skin color, fingers that change color when cold (Raynaud's phenomenon); kidney: swelling in the legs, weight gain.

Unfortunately, there is no cure for SLE. The goal of treatment is to control symptoms. Severe symptoms that involve the heart, lungs, kidneys, and other organs often need treatment from specialists. Mild forms of the disease may be treated with: NSAIDs for joint symptoms and pleurisy; corticosteroid creams for skin rashes; a drug also used to treat malaria (hydroxychloroquine); and low-dose corticosteroids for skin and arthritis symptoms. Treatments for more severe SLE may include: high-dose corticosteroids and cytotoxic drugs (drugs that block cell growth or drugs which dampen or suppress the immune system). Side effects from these drugs can be severe.

Interferon Regulatory Factor 5 (IRF5)

Interferon regulatory factor 5 (IRF5) is a transcription factor that regulates key signaling pathways that result in proinflammatory cytokine expression, including but not limited to type I interferons, interleukin (IL)-12, IL-6 and tumor necrosis factor (TNF)-α. Numerous genome wide association studies (GWAS) have reported that IRF5 polymorphisms are associated with an increased risk of the autoimmune disease SLE (Xu et al., (2013) Expert Rev Mol Med 15: e6. doi: 10.1017/erm.2013.7). IRF5 has become a putative target for the regulation of autoimmune pathology. Pre-clinical data provides compelling rationale that blocking IRF5 function may be beneficial to SLE patients as IRF5 expression is upregulated and the protein overactivated in primary immune cells from SLE patients (Feng et al. (2010) *Arthritis Rheum* 62, 562-573; Stone et al. (2012) *Arthritis Rheum* 64:788-798; Stone et al. (2013) *PLoS ONE* 8: e54487; Niewold et al. (2008) *Arthritis Rheum* 58, 2481-2487; Hedl M, Abraham C. (2012) *J Immunol.* 188, 5348-5356). The only current tools available for pre-clinical target evaluation are the use of siRNA targeting IRF5 or Irf5 transgenic knockout mice. Importantly, published studies from Irf5 knockout mice confirm that loss of Irf5 expression, and therefore function, protects mice from SLE disease onset, supporting the hypothesis that inhibiting IRF5 function will be beneficial to SLE patients (Feng et al. (2012) *Eur J Immunol* 42(6):1477-87; Yang et al. (2012) *J Immunol* 189:3741-3750).

Human IRF5 is constitutively expressed in cells of the immune system, particularly plasmacytoid dendritic cells, monocytes, and monocyte-derived dendritic cells, as well as activated B cells. IRF5 exists as multiple alternatively spliced variants resulting in the expression of a variety of isoforms each with distinct regulation, cellular localization and function. IRF5 is primarily a cytoplasmic protein in unstimulated cells that becomes post-translationally modified after stimulation with virus, Toll-like receptor ligands, DNA damage or TNF-related apoptosis inducing ligand (TRAIL) resulting in nuclear translocation and the induction of IRF5 target genes (Barnes et al. (2002) *Mol Cell Biol* 22, 5721-5740). Upon post-translational modification, IRF5 forms homodimers which have also been considered to reflect "activation"; however, homodimer formation does not ensure IRF5 nuclear translocation (Cheng et al. (2006) *J Immunol* 176, 7462-7470; Foreman et al. (2012) *PLoS ONE* DOI: 10.1371/journal.pone.0033098). IRF5 is only truly "activated" and functional once it translocates from the cytoplasm to the nucleus (Barnes et al. (2002)*Mol Cell Biol* 22, 5721-5740). IRF5 has also been shown to regulate the expression of cytokines/chemokines with lymphocyte-chemotactic activities, e.g., RANTES, MIP1α/β, MCP-1, I-309, IL8, IP10, and CXCL13, and to mediate cellular apoptosis.

Interferon regulatory factor 5 (IRF5) polymorphisms as well as IRF5 activity are considered viable markers of systemic lupus erythematosus (SLE) disease activity and severity. IRF5 is constitutively activated in SLE monocytes (Stone et al. (2012) *Arthritis Rheum* 64:788-798) and in SLE B cells. IRF5 is proposed to be a viable target in other autoimmune diseases. The inhibitors described herein are useful to study IRF5 function in primary human immune cells and to determine the potential effects of inhibiting IRF5 in patients. As described herein, IRF5 polymorphisms contribute to risk of numerous autoimmune diseases, including but not limited to rheumatoid arthritis, inflammatory bowel syndrome and multiple sclerosis. As such, tools that specifically target IRF5 activation and therefore function, will be valuable across numerous fields and diseases, for example, for studying and/or treating autoimmune diseases such as systemic lupus erythematosus (SLE), systemic sclerosis (scleroderma), polymyositis/dermatomyositis, Crohn's disease, rheumatoid arthritis, periodontitis, SLE-associated atherosclerosis, Sjögren's syndrome, autoimmune encephalomyelitis, sarcoidosis, Behçet's disease, myasthenia gravis, lupus nephritis, inflammatory bowel disease, ankylosing spondylitis, primary biliary cirrhosis, colitis, juvenile idiopathic arthritis, pulmonary fibrosis, antiphospholipid syndrome and psoriasis. Other non-autoimmune diseases that may be studied and/or treated include classical Hodgkin lymphoma, atherosclerosis, cardiovascular disease, neuropathic pain, and some types of leukemia and lymphoma, such as T cell large granular lymphocyte leukemia.

As described in the Examples, the inhibitors have been evaluated in a variety of different cellular assays, as well as in an animal model of SLE (see, e.g., Heyler and Howie, *Nature* (1963) 4863:197; Theofilopoulos and Dixon, *Adv Immunol* (1985) 37:269-390). The inhibitors are selective for IRF5 and not other IRF family members. The stability of the inhibitors has been examined over time in cell culture and are found to be stable over 72 hours. FITC-conjugated inhibitors are detected at 72 hours post-incubation in PBMCs.

As described herein, the inhibitors comprise a cell penetration sequence and an IRF5 NLS sequence. Accordingly, these inhibitors are non-naturally occurring peptides that are not products of nature. Additionally, the inhibitors described herein comprise markedly different characteristics (e.g., structural, functional and/or other properties) as compared to naturally occurring peptides that comprise an IRF5 NLS sequence or a cell penetration sequence.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA that can be single-stranded or double-stranded, optionally containing synthetic, non-natural or altered nucleotide bases capable of incorporation into DNA or RNA polymers. The terms "nucleic acid," "nucleic acid molecule," or "polynucleotide" are used interchangeably.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

"Amino acid" or "amino acid sequence" include an oligopeptide, peptide, polypeptide, or protein sequence, or to a fragment, portion, or subunit of any of these, and to naturally occurring or synthetic molecules. The terms "polypeptide" and "protein" include amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. Capitalized, single-letter abbreviations of the amino acids refer to the natural L-isomer. Lower case, single-letter abbreviations of the amino acids denotes the D-isomer.

The terms "polypeptide," "peptide," and "protein" are used interchangeably to refer to polymers of amino acids of any length. In certain embodiments, peptides and polypeptides may be entirely composed of natural peptide amino acids, be entirely composed of synthetic, non-natural analogues of amino acids, or, may be a chimeric molecule of partly natural peptide amino acids and partly non-natural analogs of amino acids. In one aspect, a polypeptide is used in a composition, cell system or process of the invention. In addition, polypeptide can refer to compounds comprised of polymers of amino acids covalently attached to another functional group (e.g., a label, solubilizing group, a targeting group, PEG, non-amino acid group, or other therapeutic agent). In certain embodiments, a polypeptide of the invention may be operably linked to a label (e.g., through a direct bond or through a linking group), such as a flourescent label or a radiolabel; the labeled peptides may be used for diagnostic imaging, research or therapeutic purposes. Unless stated otherwise, peptide sequences are shown with the N'terminus on the left and the C'terminus on the right.

The invention encompasses isolated or substantially purified protein compositions. In the context of the present invention, an "isolated" or "purified" polypeptide is a polypeptide that exists apart from its native environment and is therefore not a product of nature. The terms "polypeptide" and "protein" are used interchangeably herein. An isolated protein molecule may exist in a purified form or may exist in a non-native environment such as, for example, a transgenic host cell or bacteriophage. For example, an "isolated" or "purified" protein, or biologically active portion thereof, is substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed proteins or partial-length proteins encoded thereby are also encompassed by the present invention. By "fragment" or "portion" is meant a full length or less than full length of the amino acid sequence of a protein.

The genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

Polypeptide compositions of the invention can contain any combination of non-natural structural components. Accordingly, a polypeptide of the invention may comprise a chemical modification. For example, the polypeptide may comprise one or more synthetic non-natural peptide amino acids. Additionally, the linking group joining individual peptide residues or the peptide scaffold may be chemically modified as described below. Individual peptide residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH2- for —C(=O)—NH—), aminomethylene (CH2-NH), ethylene, olefin (CH=CH), ether (CH2-0), thioether (CH2-S), tetrazole, thiazole, retroamide, thioamide, or ester (see, e.g., Spatola (1983) in Chemistry and Biochemistry of Amino Acids, Peptides and Proteins, Vol. 7, pp. 267-357, "Peptide Backbone Modifications," Marcel Dekker, N.Y., incorporated herein by reference). Non-natural scaffolds may also be used to stabilize a polypeptide described herein. For example, hydrocarbon bridges can be used to crosslink side chains (hydrocarbon-stapled or hydrogen bond surrogate alpha-helices); terphenyls may be added, beta amino acids may be included to generate a beta-peptide and/or a peptoid, mini protein may be generated. Accordingly, in certain embodiments of the invention, a polypeptide described herein may be chemically modified (i.e., comprise a non-natural structural component). In certain embodiments, the chemical modification stabilizes the polypeptide.

Polypeptides used to practice methods of the invention can be modified by either natural processes, such as post-translational processing (e.g., phosphorylation, acylation, etc), or by chemical modification techniques, which result in a modified polypeptide. Modifications discussed herein can occur anywhere in the polypeptide, including the peptide backbone, the amino acid side-chains and the amino or carboxyl terminus. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, PEGylation, proteolytic processing, phosphorylation, prenylation, selenoylation, sulfation, and transfer-RNA mediated addition of amino acids to protein such as arginylation. See, e.g., Creighton, T. E., Proteins-Structure and Molecular Properties 2nd Ed., W. H. Freeman and Company, New York (1993); Posttranslational Covalent Modification of Proteins, B. C. Johnson, Ed., Academic Press, New York, pp. 1-12 (1983), incorporated herein by reference.

The following terms are used to describe the sequence relationships between two or more sequences: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA, gene sequence or peptide sequence, or the complete cDNA, gene sequence or peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, J M B, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity. Such implementations include, but are not limited to: CLUSTAL; the ALIGN program and GAP, BESTFIT, BLAST, FASTA, and TFASTA. Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)).

Software for performing BLAST analyses is publicly available through the National Center for Biotechnology Information. In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST can be utilized. Alternatively, PSI-BLAST can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of sequences means that a molecule comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

Certain embodiments of the invention provide an expression cassette comprising a nucleic acid molecule described herein. In certain embodiments, the expression cassette described herein further comprises a promoter, such as a regulatable promoter or a constitutive promoter. Examples of suitable promoters include a CMV, RSV, pol II or pol III promoter. The expression cassette may further contain a polyadenylation signal (such as a synthetic minimal polyadenylation signal) and/or a marker gene. Certain embodiments of the invention provide a vector comprising an expression cassette described herein.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional peptide of interest, for example a polypeptide described herein. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., 1995).

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

In one embodiment, the phrase "selectively binds" means that a polypeptide made or used in the present invention preferentially binds to one type of interferon regulatory factor (IRF) over another type when in the presence of a mixture of two or more forms of IRF (e.g., a polypeptide selectively binds to IRF5 over another IRF form).

"Operably-linked" refers to the association two chemical moieties so that the function of one is affected by the other, e.g., an arrangement of elements wherein the components so described are configured so as to perform their usual function.

"Systemic delivery," as used herein, refers to delivery that leads to a broad biodistribution of an active agent (e.g., the inhibitors described herein) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of agents can be by any means known in the art including, for example, intravenous, subcutaneous, and intraperitoneal. In a preferred embodiment, systemic delivery is by intravenous delivery.

"Local delivery," as used herein, refers to delivery of an active agent such to a target site within an organism. For example, an agent can be locally delivered by direct injection into a disease site, other target site, or a target organ such as the liver, heart, pancreas, kidney, and the like.

The terms "treat" and "treatment" refer to both therapeutic treatment and prophylactic or preventative measures, wherein the object is to prevent or decrease an undesired physiological change or disorder, such as the development of an autoimmune disease or other disease/disorder discussed herein. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

Administration

A polypeptide of the invention can be formulated as a pharmaceutical composition and administered to a mammalian host, such as a human patient in a variety of forms adapted to the chosen route of administration, i.e., orally or parenterally, by intravenous, intramuscular, topical or subcutaneous routes.

Thus, the present polypeptides may be systemically administered, e.g., orally (e.g., added to drinking water), in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polypeptide may be combined with one or more excipients and used in the form of ingestible tablets, buccal tablets, troches, capsules, elixirs, suspensions, syrups, wafers, and the like. Such compositions and preparations should contain at least 0.1% of the polypeptide. The percentage of the compositions and preparations may, of course, be varied and may conveniently be between about 2 to about 60% of the weight of a given unit dosage form. The amount of polypeptide in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polypeptide, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptide may be incorporated into sustained-release preparations and devices.

The polypeptide may also be administered intravenously or intraperitoneally by infusion or injection. Solutions of the polypeptide or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polypeptide in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present polypeptides may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present polypeptides can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions, which can be used to deliver the polypeptides to the skin, are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the polypeptides can be determined by comparing their in vitro activity, and in vivo activity in animal models. Methods for the extrapolation of effective dosages in mice, and other animals, to humans are known to the art; for example, see U.S. Pat. No. 4,938,949.

The amount of the polypeptides, or an active salt or derivative thereof, required for use in treatment will vary not only with the particular salt selected but also with the route of administration, the nature of the condition being treated and the age and condition of the patient and will be ultimately at the discretion of the attendant physician or clinician.

The polypeptides may be conveniently formulated in unit dosage form. In one embodiment, the invention provides a composition comprising a polypeptide formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The polypeptides of the invention can also be administered in combination with other therapeutic agents, for example, other agents that are useful for treating autoimmune diseases, classical Hodgkin lymphoma, atherosclerosis, cardiovascular disease, neuropathic pain, or certain amenable types of leukemia and lymphoma, such as T cell large granular lymphocyte leukemia. Accordingly, in one embodiment the invention also provides a composition comprising a polypeptide described herein, at least one other therapeutic agent, and a pharmaceutically acceptable diluent or carrier. The invention also provides a kit comprising a polypeptide of the invention, at least one other therapeutic agent, packaging material, and instructions for administering the polypeptide and the other therapeutic agent or agents to an animal to treat an autoimmune disease, classical Hodgkin lymphoma, atherosclerosis, cardiovascular disease, neuropathic pain, or certain amenable types of leukemia and lymphoma, such as T cell large granular lymphocyte leukemia.

Certain embodiments of the invention will now be illustrated by the following non-limiting Examples.

Example 1

Little is known of the mechanism(s) regulating IRF5 nuclear localization. Two functional nuclear localization signals (NLS) were identified and characterized in the IRF5 protein that were not conserved or homologous with NLS in other IRFs. The IRF5 poylpeptide contains two NLSs, one residing in the amino-terminus (PRRVRLK) (SEQ ID NO: 1), and the other in the carboxyl-terminus (PREKKLI) (SEQ ID NO:2) (Barnes et al. (2002) *Mol Cell Biol* 22, 5721-5740). While both NLSs could signal translocation to the nucleus, each had a distinct function. The amino-terminal NLS, located in the DNA binding domain, contributed to nuclear localization and retention, while the carboxyl-terminal NLS was responsive to virus-induced nuclear translocation but not retention. These two NLSs are solely responsible for nuclear localization and transactivation of target promoters as a mutant lacking both NLSs was localized in the cytoplasm and non-functional (Barnes et al. (2002) *Mol Cell Biol* 22, 5721-5740). Data from crystallography studies (Chen et al. (2008) *Nat Struct Mol Biol* 15, 1213-1220) and mutational analyses (Barnes et al. (2002) *Mol Cell Biol* 22, 5721-5740) indicate that the amino-terminal NLS is masked by an intramolecular interaction or association with another protein and post-translational modification is necessary for exposure and retention of IRF5 in the nucleus, along with enhancement of its transactivating potential. IRF5 also contains a functional nuclear export signal that controls shuttling between the cytoplasm and nucleus. As described herein, cell permeable peptide inhibitors directed at each of these NLS were designed in order to specifically inhibit IRF5 nuclear translocation.

The amino (5')- and carboxyl (3')-terminal NLS sequences of IRF5, along with additional controls to confirm specific peptide function versus non-specific cationic peptide function (Table 1), were synthesized and conjugated to a protein transduction (PTD) sequence in order to render the peptide cell permeable (Bowdish et al. (2004) *J Immunol* 172, 3758-3765). NLS sequences are cationic peptides that accumulate within cells when added exogenously. Peptide sequences were synthesized using LifeTein Peptide Synthesis Services. Peptides were solubilized in PBS and tested over a concentration range (0.025, 0.25, 2.5 and 25 µM) in human immortalized and/or primary cells.

TABLE 1

IRF5 NLS peptide inhibitors and controls.

| | |
|---|---|
| IRF5 5'NLS | DRQIKIWFQNRRMKWKK<u>PRRVRLK</u> (SEQ ID NO: 3) |
| IRF5 3'NLS | DRQIKIWFQNRRMKWKK<u>PREKKLI</u> (SEQ ID NO: 4) |
| PTD | DRQIKIWFQNRRMKWKK (SEQ ID NO: 5) |
| Scrambled 5'NLS | DRQIKIWFQNRRMKWKK<u>PKRRRLV</u> (SEQ ID NO: 6) |
| Scrambled 3'NLS | DRQIKIWFQNRRMKWKK<u>PIKRLKE</u> (SEQ ID NO: 7) |

FITC (Fluorescein isothiocyanate)-conjugated peptides were synthesized to examine cell penetrance by fluorescent microscopy and flow cytometry. In general, cells were incubated with inhibitors for 4 hours before analysis or stimulation. Inhibitor titrations, cytotoxicity, and cell cycle assays were performed to determine the optimal inhibitor concentration that does not affect cell growth. The ability of each peptide to inhibit IRF5 nuclear localization was then determined on the Amnis Imagestream imaging flow cytometer. Example 4 also describes similar experiments (see, FIGS. 1A-C and 2A-B).

Example 2

The transcription factor interferon regulatory factor 5 (IRF5) has previously been implicated in the onset of the autoimmune disorder systemic lupus erythrematosus (SLE). Elevated levels of inflammatory cytokines are a common characteristic of SLE, and are believed to contribute to both autoantibody production and wide spread inflammation. Upon activation, cytoplasmic IRF5 translocates to the nucleus to initiate pro-inflammatory gene transcription. To achieve nuclear translocation, IRF5 relies on two nuclear localization signals located in the N' and C' termini of the protein. To investigate the therapeutic potential of IRF5 inhibition, two unique cell-penetrating peptides have been developed (SEQ ID NO:3 and SEQ ID NO:4). Upon treatment with these inhibitors, IRF5 is excluded from the nucleus, while IRF7 and NFκB nuclear translocation were unaffected following activation. The impact of IRF5 inhibition has also been investigated in a variety of cell lines as well as primary peripheral blood mononuclear cells. The inhibitors show no impact on cell cycle, viability, or IRF5 protein levels. As IRF5 has been linked to expression of IgG subtypes in mice, the IRF5 inhibitors were used to examine the impact of IRF5 inhibition in the Ramos B cell line. Interestingly, no impact of the inhibitors on surface IgG expression was found. In THP1 cells, however, a marked reduction in inflammatory cytokine expression was seen following stimulation with LPS and IFNγ. These data highlight the usefulness of targeting IRF5 in order to reduce the inflammatory signature characteristic of SLE patients.

Example 3

The transition of naïve B cells to effector B cells is dependent on a large transcription factor network, which mediates both effector B cell differentiation and function. The full repertoire of transcription factors involved in this process is not known, yet dysregulation of this transcription factor network can result in altered B cell function and autoimmunity. It appears that the transcription factor, interferon regulatory factor 5 (IRF5), is involved in the development of effector B cells. Irf5$^{-/-}$ mice have previously been reported to have reduced plasma B cells, as well as reduced serum IgG subtypes. It remains unclear, however, what role IRF5 may play in human B cell development and function. Significant levels of IRF5 in B cells translocate to the nucleus following stimulation with anti-IgM antibody and CpG. In order to characterize the role of IRF5 in human B cells, IRF5 ChIP-Seq have been performed in both primary naïve B cells and Ramos B cells either mock or anti-IgM and CpG treated. Genes associated with plasma B cell development were significantly enriched following activation, suggesting IRF5 plays a critical role in the differentiation of plasma B cells. To further characterize the role of IRF5 in primary human B cells, siRNA-mediated knockdown of IRF5 has been performed. Knockdown of IRF5 did not show significant impact on cell viability, however, reduced inflammatory cytokine expression, decreased plasmablast differentiation, and decreased IgG subtype production were seen. These data highlight the multi-functional role of IRF5 in regulating both human B cell differentiation and function.

Example 4

Patients and Methods

Human Peripheral Blood Mononuclear Cell (PBMC) isolation. Approximately 200-350 milliliters (mLs) of blood was drawn from consented donors and subsequently diluted 1:1 with PBS without Calcium or Magnesium (PBS—$Ca^{2+}$—$Mg^{2+}$). Alternatively, prepared buffy coats isolated from healthy donors were purchased from the New York Blood Center and diluted 2-fold in PBS—$Ca^{2+}$—$Mg^{2+}$. Approximately 35 mLs of diluted blood was layered onto 15 mLs of Ficoll at room temperature in 50 mL tubes. The blood Ficoll suspension was then centrifuged for 30 minutes at 400 G with no brake at 21° C. in a swing bucket centrifuge. Following centrifugation, the serum layer was removed through pipet aspiration and the buffy coat layer transferred to a fresh 50 mL tube. The resulting buffy coat layer was washed two times in PBS—$Ca^{2+}$—$Mg^{2+}$ and resuspended in PBS—$Ca^{2+}$—$Mg^{2+}$ supplemented with 5% FBS. Isolated PBMCs were immediately utilized for B cell experiments. All experiments were approved by the Rutgers Biomedical and Health Sciences IRB and the Feinstein Institute for Medical Research IRB. Informed consent was obtained from all healthy donors and experiments were performed in accordance with Institution guidelines.

Peptide inhibitor titration and uptake. Ramos B cells or THP1 cells were treated with 0.025, 0.25, 2.5, and 25 uM of FITC conjugated peptide inhibitors for 2 hours. Cells were washed, stained with propidium iodide, and immediately analyzed by flow cytometry for uptake of FITC peptide. For uptake experiments in PBMCs, cells were incubated with 10 uM of either mock, scrambled, N-term' NLS, or C-term' NLS FITC conjugated inhibitor for 2 hours. Cells were then washed and blocked as previously outlined, and subsequently stained with CD19-BV510 and CD14-PE (Biolegend Catalog #301806). Cells were fixed, stained with DRAQ5 nuclear dye and analyzed by imagestream for uptake of FITC peptide.

Quantitative Real-Time PCR. RNA was prepared from nucleofected primary B cells by Trizol® (guanidinium thiocyanate-phenol-chloroform extraction method) isolation. Following RNA isolation, cDNA was prepared followed by quantitative real-time PCR (qPCR) using specific primer sets. Each sample was assayed in replicates of three, per primer set used. The threshold values ($C_T$) were averaged over each sample replicated, followed by normalization via the $\Delta\Delta C_T$ method to a housekeeping gene such as Beta-actin.

Imaging Flow Cytometry. PBMCs were isolated as previously outlined, and treated with inhibitor for 1-2 hours, followed by stimulation with R848 (500 ng/mL) or SLE Serum (2%). PBMCs were then stained for CD19 (BD Biosciences Catalog #: 562847) or CD14 (Biolegend Catalog #: 301806) for 1 hour, after which, cells were fixed overnight in 1% paraformaldehyde. The following day cells were and permeabilized in 0.1% Triton-X-100. Permeabilized cells were blocked in 5% BSA solution and subsequently stained for IRF5 (Abcam Catalog #: ab193245). Cells were washed and fixed in 1% paraformaldehyde. Prior to acquisition, the nuclear dye DRAQ5 was added at a 1:50 dilution. Images were acquired on the Amnis Image Stream using the 40× objective. Nuclear translocation was quantified in the Amnis IDEAS software suite. Cells were first filtered through the brightfield area vs brightfield aspect ratio gate to exclude non-viable and doublet events. Following which a similar gate of the DRAQ5 nuclear channel was used. This added an extra measure of stringency for cell viability. Images were gated on either $CD14^+$ $IRF5^+$ or $CD19^+$ $IRF5^+$ events, followed by gating on images with a Gradient RMS of greater than 20 on the DRAQ5 channel. This was done to select images with a high level of clarity. Finally, IRF5 nuclear translocation was determined through use of the similarity score feature contrasting IRF5 staining with DRAQ5 staining. A similarity score of greater than or equal to 2 was considered a translocation event.

Cell Fractionation. Cells were fractionated according to manufacturer's protocol (Cell Signaling, Cell fractionation kit, #9038). Following fractionation, lysates were sonicated and boiled. Nuclear fraction was analyzed by Western blot as follows: 30 µL of lysate was loaded onto a 3-8% NuPAGE® Novex® Tris-Acetate gel (Life Technologies, #EA0378BOX), and transferred onto a 0.45 µm nitrocellulose membrane (Bio-Rad Laboratories). Membrane was blocked in TBS/0.25% Tween 20 containing 5% BSA for 1 h at RT and incubated overnight at 4° C. with α-IRF5 antibody (Cell Signaling, #13496) followed by HRP-conjugated secondary antibody (Cell Signaling, α-rabbit #7074S). The nuclear fraction was confirmed using Lamin B1 (Cell Signaling, #15068). Membrane was incubated with Clarity™ ECL Western Blotting Substrate (Bio-Rad Laboratories) and chemiluminescence detected with a ChemiDoc™ MP Imaging System (Bio-Rad Laboratories). The PageRuler™ Plus Prestained Protein Ladder (ThermoFisher Scientific) was used for size reference.

Statistical Analysis. For experiments shown, >=3 experimental replicates were used unless otherwise noted. Student's t-test was used for comparisons between two samples with normal distribution. Prior to test, graph kurtosis was analyzed to ensure normal distribution. For comparisons of one factor over multiple groups, One-Way ANOVA was performed with Tukey's post-hoc test for significance. For comparisons of multiple factors over multiple groups, Two-Way ANOVA was performed with Tukey's post-hoc test for significance.

Results

Design of IRF5 Peptide Inhibitors. Given the association of IRF5 with the onset of several autoimmune disorders, as well as work that has been done in establishing the role of IRF5 in B cell proliferation and antibody production, it was investigated whether therapeutic inhibition of IRF5 nuclear translocation was feasible. To accomplish this, peptide inhibitors of the IRF5 amino (N')-terminal and carboxyl (C')-terminal nuclear translocation signals (NLS) were designed. Precedence for this strategy comes from previous NFκB inhibitors, which have been proven to be effective in inhibiting NFκB-mediated transcriptional activity (Lin, Y. Z., et al., J Biol Chem, 1995. 270 (24): p. 14255-8; Mallavia, B., et al., Am J Pathol, 2013. 182 (5): p. 1910-21; Orange, J. S. and M. J. May, Cell Mol Life Sci, 2008. 65 (22): p. 3564-91; Zhang, L., et al., Proc Natl Acad Sci USA, 1998. 95 (16): p. 9184-9). To transduce the cell membrane, IRF5 NLS sequences were combined with a protein transduction domain (PTD). The PTD has been previously shown to facilitate cell permeability of small peptides (see, Orange, J. S. and M. J. May, Cell Mol Life Sci, 2008. 65 (22): p. 3564-91). Design of the N'-terminal NLS inhibitor was accomplished by merging the PTD sequence "DRQIKIWFQNRRMKWKK (SEQ ID NO:5)" with the IRF5 NLS sequence of "PRRVRLK (SEQ ID NO: 1)". The N'-terminal NLS sequence used corresponded to amino acids 12 thru 18 of IRF5 variant 5. A similar strategy was used for the C'-terminal NLS inhibitor, whereby the PTD sequence was merged with the "PREKKLI (SEQ ID NO:2)" C'-terminal NLS sequence, corresponding to amino acids 408 thru 441 of IRF5 variant 5. A control peptide of the PTD sequence alone and one merged to a scrambled NLS sequence of "PKRRRLV (SEQ ID NO:8)" were also designed (see, Table 1).

Figure 1D:
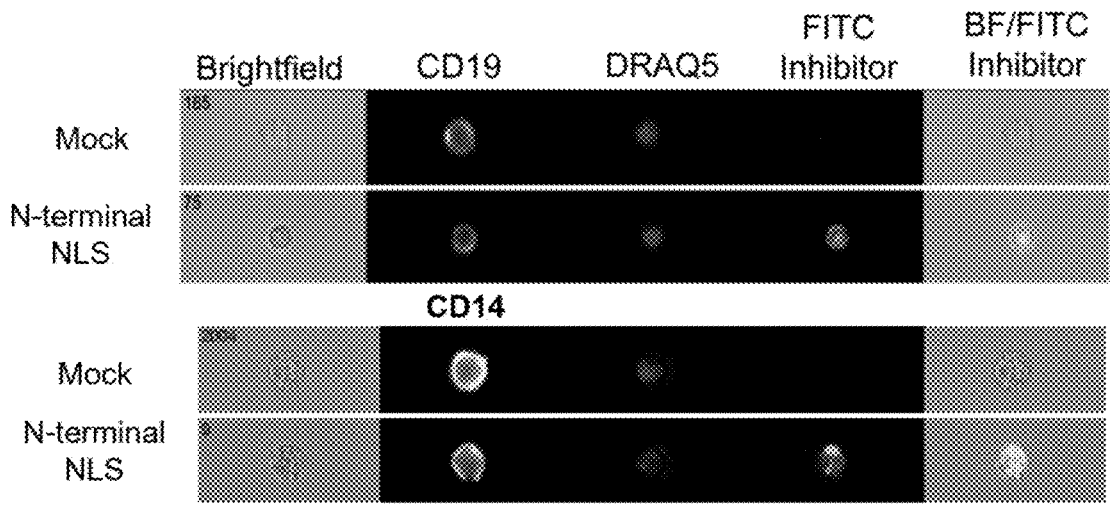
Figure 1E:
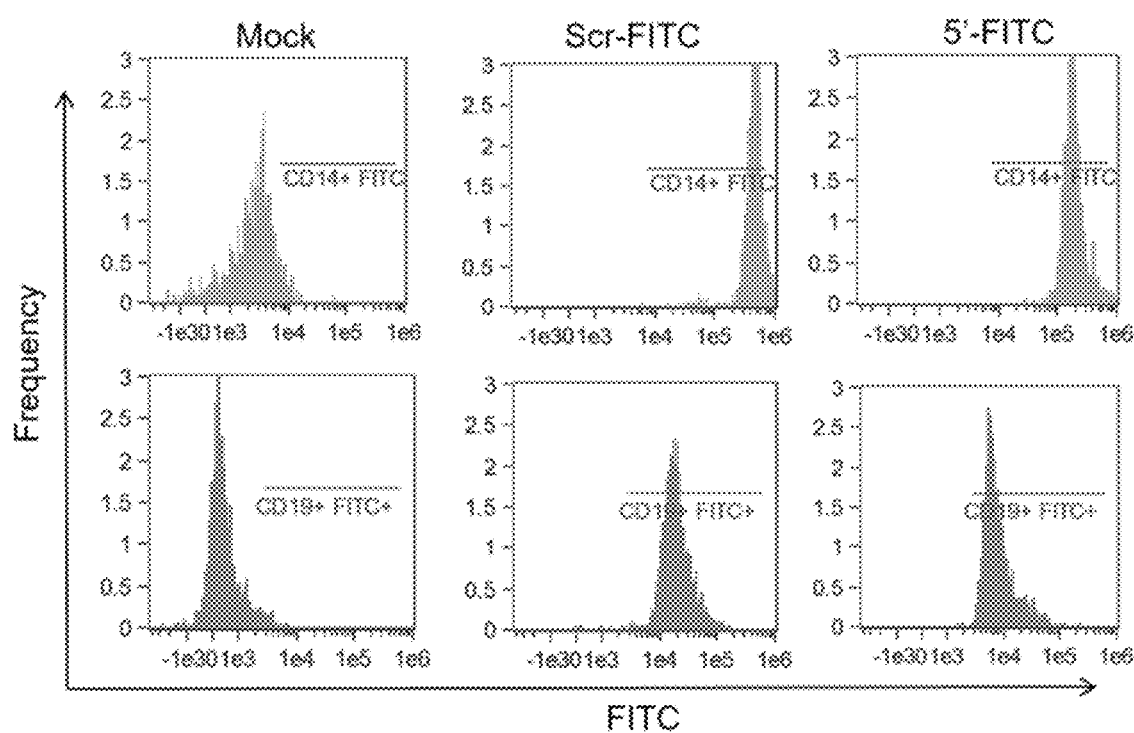

IRF5 Peptide Inhibitors readily enter the cell and have low associated toxicity. IRF5 peptide inhibitors were conjugated to FITC moieties to measure cellular uptake over a dose-dependent response. Ramos B cells were treated with increasing concentrations of FITC-conjugated inhibitor for 2 hours. Cells were washed and subsequently treated with propidium iodide to quantify cell death. While at the lower doses of 0.025 and 0.25 uM minimal uptake was seen, at 2.5 uM however, greater than 95% of cells were positive for the FITC-conjugated inhibitor (FIG. 1A). In addition, less than 3% of cells stained positive for propidium iodide, indicating low toxicity for the inhibitor at this dose. At the 25 uM dose, greater than 90% of cells had taken up the inhibitor, while both scrambled and N'-terminal inhibitors showed minimal associated toxicity. However, no significant increase in uptake was seen between 2.5 uM and 25 uM concentrations of inhibitor. To ensure no impact on cell viability from treatment with the inhibitors, Ramos B cells were treated with varying concentrations of inhibitor as used previously for the titration experiments for 24 hours, and tryphan blue staining was subsequently performed. Similar to our previous titration results, minimal toxicity associated with the inhibitors was observed at concentrations up to 2.5 uM. However, at 25 uM a decrease in viability was noted for the scrambled inhibitor (FIG. 1B). Additionally, to ensure the peptide inhibitors did not have significant off target effects, measured cell cycle progression was measured in Ramos B cells following treatment with increasing concentrations of inhibitor. Cell cycle was measured through propidium iodide incorporation, and quantified through flow cytometry. No significant difference in cell cycle progression was seen at any of the dosages of the peptide inhibitor (FIG. 1C). Next, the uptake experiments in primary peripheral blood mononuclear cells isolated from healthy donors was sought to be confirmed. Therefore, imaging flow cytometry was utilized to confirm uptake of the inhibitors in primary PBMCs, followed by gating on B cells and monocytes. Isolated PBMCs were treated with 2.5 uM of either mock, N'-terminal, or Scrambled NLS inhibitors for an hour, and subsequently stained with CD19 to demarcate B cells and CD14 to identify monocytes. Both B cells and monocytes had indeed successfully taken up the peptide inhibitor within 1 hour (FIG. 1D). Interestingly, monocytes showed a much higher level of uptake than that seen in B cells. To determine if it would be possible to increase uptake of the inhibitor in B cells, uptake following incubation with 10 uM for 1 hour was measured. B cells showed a slight increase in uptake following treatment with 10 uM of inhibitor, while monocytes continued to have higher levels of uptake than B cells. This suggested it may be possible to achieve cell type-specific activity of the inhibitor through varied dosage.

IRF5 peptide inhibitor blocks IRF5 nuclear translocation in both B cells and monocytes. IRF5 nuclear translocation has been shown to be consequential to increased IFN secretion and antibody production, therefore, inhibition of nuclear translocation would have significant therapeutic value. As IRF5 has been implicated in the onset of autoimmune diseases in both monocytes and B cells, it was sought to be determined if IRF5 nuclear translocation could be inhibited in both cell populations following stimulation with the TLR7 agonist R848. Due to the use of PBMCs, R848 was utilized for stimulation as it is recognized by TLR7 on both monocytes and B cells. Isolated PBMCs were cultured in the presence of either mock, scrambled, N'-terminal, or C'-terminal NLS inhibitor for 1 hour followed by stimulation with 500 ng/mL of R848 for 2 hours. A significant reduction in IRF5 nuclear translocation was seen in both monocytes and B cells following treatment with the N'-terminal NLS inhibitor in comparison to the scrambled control (FIG. 2A,B). Representative images are shown in FIG. 2C. In monocytes, roughly a 3-fold reduction, and an approximate 2-fold reduction in B cells was seen between scrambled control and the N'-terminal inhibitor. In contrast, the —C'-terminal inhibitor showed only slightly reduced nuclear translocation in monocytes that failed to achieve significance, while in B cells, the C'-terminal inhibitor showed no inhibition of IRF5 nuclear translocation. To further confirm a block in nuclear translocation of IRF5, cell fractionation was performed on isolated primary monocytes which were treated with inhibitor and subsequently stimulated with R848. Reduced levels of IRF5 were seen in the nucleus in the presence of either the N'- or C'-terminal inhibitors (FIGS. 2D,E).

IRF5peptide inhibitors are specific to IRF5. As inhibition of IRF5 activity achieved through the peptide inhibitors may rely on saturation of nuclear translocation machinery, it remained possible other transcription factors would be similarly impacted. Specifically, transcription factors which require nuclear translocation and have overlapping transcriptional targets with IRF5, such as NFκB, seemed to be the most logical candidates to assay. Therefore, we examined NFκB nuclear translocation following treatment with the IRF5 peptide inhibitors and subsequent R848 stimulation in both B cells and monocytes. No significant impact was seen on NFκB nuclear translocation in either B cells or monocytes in the presence of the inhibitor (FIG. 3A). Overall nine IRF transcription factors exist in humans, with all nine having high similarity. To determine if other members of the IRF family of transcription factors were impacted by the IRF5 peptide inhibitors, nuclear translocation of another IRF transcription factor important in inflammatory cytokine expression was measured. IRF7 is known to be important in regulating interferon secretion in plasmacytoid dendritic cells (pDCs), with overlapping functions with IRF5. Therefore, IRF7 nuclear translocation was quantified in pDCs following treatment with the inhibitors and also stimulation with R848. No significant impact was seen on IRF7 nuclear translocation (FIG. 3B).

IRF5 peptide inhibitors reduce expression of inflammatory cytokine expression. Immediately following nuclear translocation, IRF5 upregulates pro-inflammatory cytokine expression in both monocytes and B cells. In SLE it is believed that increased levels of inflammatory cytokines contribute to altered B cell differentiation, as well as increased systemic inflammation (Banchereau, J. and V. Pascual, Immunity, 2006. 25 (3): p. 383-92; Tackey, et al., Lupus, 2004. 13 (5): p. 339-43). It has been previously shown that both monocytes and B cells release elevated levels of inflammatory cytokines such as IL6 (Stone, R. C., et al., Arthritis Rheum, 2012. 64 (3): p. 788-98; Tackey, et al., Lupus, 2004. 13 (5): p. 339-43). Therefore, blockade of IRF5 nuclear translocation should ultimately impact inflammatory cytokine production. IL6 and IL10 production were initially examined in the Ramos B cell and THP monocyte cell lines, following stimulation. Both Ramos and THP1 cell lines were pre-treated with inhibitor for 1 hour, followed by LPS stimulation of THP1 cells and anti-IgM plus CpG-B stimulation of Ramos B cells for 2 hours. For both cell types, IL6 and IL10 production were most significantly reduced following treatment with the N'-terminal inhibitor (data not shown). In the case of monocytes, a 2-fold inhibition of IL6 expression was seen, whereas in Ramos B cells, a 3-fold reduction in expression was noted. IL6, IFNa, and IL10 production were examined next in isolated PBMCs treated with inhibitor for 1 hour, followed by R848 stimulation for 2 hours. All three cytokines were found to be significantly reduced following treatment with the N'-terminal inhibitor (FIG. 4). A 70% reduction in IL6, a 35% reduction in IL10, and a 52% reduction in IFNa expression was seen after treatment with the N'-terminal inhibitor. This demonstrates inhibition of IRF5 nuclear translocation results in a direct reduction in inflammatory cytokine expression.

Figure 5:
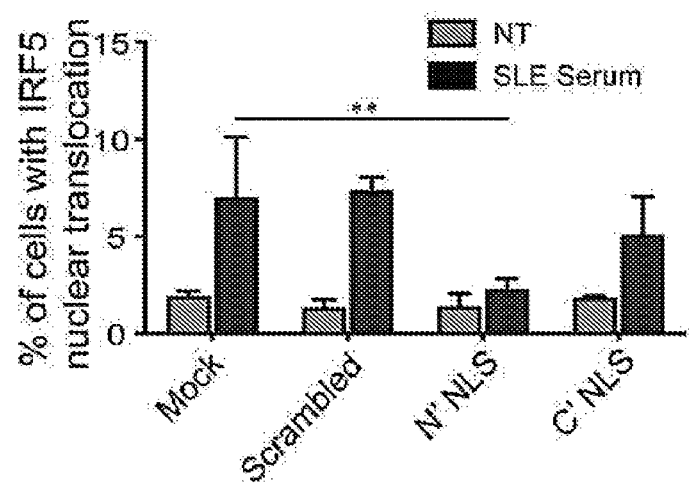
FIG. 5. IRF5 peptide inhibitors inhibit SLE serum-induced IRF5 nuclear translocation. Healthy donor PBMCs were pre-incubated with peptide inhibitors for 1 hour and then stimulated with SLE serum for 2 hours. IRF5 nuclear localization was determined in CD14+ monocytes by imaging flow cytometry.
Figure 9:
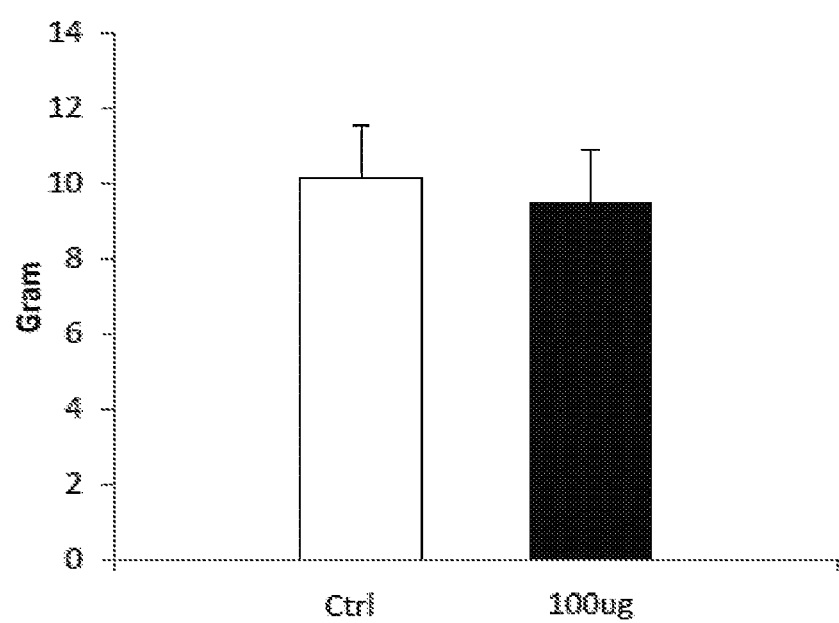
FIG. 9. Delta change of body weight at week 34. NZB/W F1 mice were IP-injected with 100 µg/day N'terminal (100 µg) or 100 µl PBS (Ctrl) at 8 weeks-old, on day 0, 1, 4, 7 and 14 (n=6/group). The delta change of body weight was calculated at week 34 in comparison to baseline (week 8).
Figure 10:
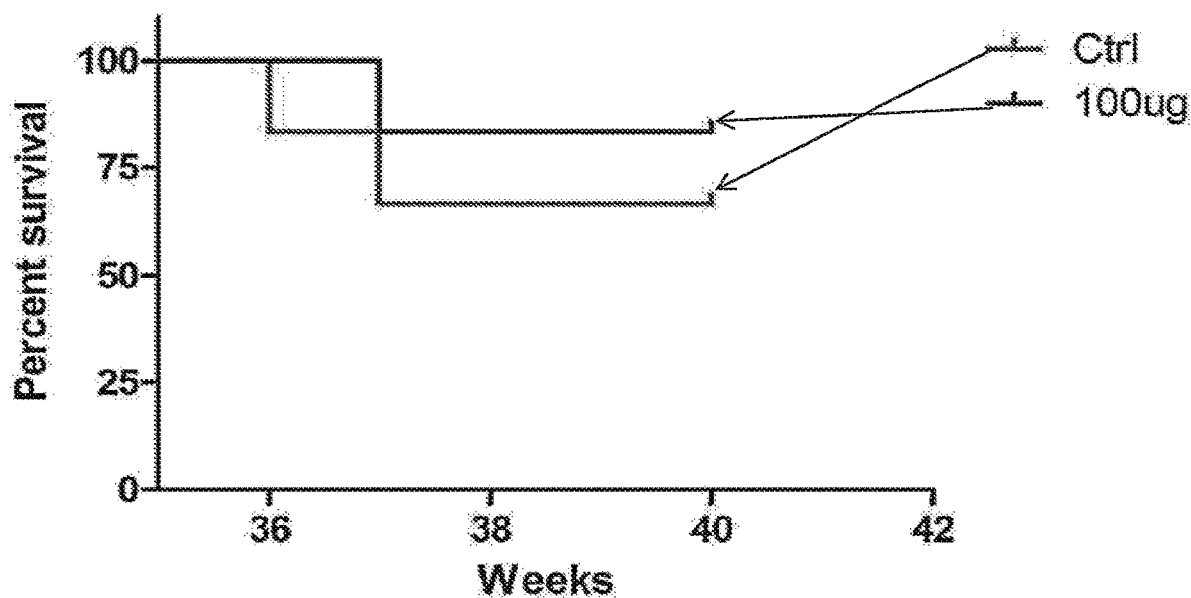
FIG. 10. Comparisons of percent survival between n=6 NZB/W F1 mice treated with N'terminal peptide and n=6 mock-treated mice. NZB/W F1 mice were IP injected with 100 µg/day N'terminal (100 µg) or 100 µl PBS (Ctrl) at 27-week age, on day 0, 1, 4, 7 and 14. Percentage of survival was sensed until week 40.

IRF5 peptide inhibitors are effective in reducing IRF5 nuclear translocation in PBMCs from SLE Patients. Serum from SLE patients results in increased IRF5 nuclear translocation following addition to healthy PBMCs. Serum stimulation of healthy PBMCs most likely triggers multiple activation pathways, and would represent a more disease relevant stimuli than those of purified TLR ligands. To determine if the peptide inhibitors described herein would be effective following addition of complex stimuli such as SLE serum, isolated PBMCs from healthy donors were treated with the peptide inhibitors followed by stimulation with SLE serum from individual patients. IRF5 nuclear translocation was again assayed through imaging flow cytometry, following which a significant reduction in IRF5 nuclear translocation was observed (FIG. 5). An inhibitor utilized for the treatment of SLE should also demonstrate an ability to block basal IRF5 nuclear translocation in SLE patients. SLE patients have been shown to have high levels of basal IRF5 nuclear translocation. To determine if these peptide inhibitors will be effective in reversing basal elevated IRF5 nuclear translocation, PBMCs will be isolated from SLE patients having SLEDAI scores=0, >0<4, >4, and with active flares. Data thus far support that pre-treatment with the inhibitors results in a significant decrease in basal IRF5 nuclear translocation in both SLE monocytes and B cells.

Example 5

In vivo murine experiments were performed using NZB/W F1 mice, which model spontaneous lupus, and the IRF5 peptide inhibitor (DRQIKIWFQNRRMKWKKPRRVRLK (SEQ ID NO:3))

(Life Tein, LLC). Specifically, treatment groups were examined at 8 weeks of age and at 27 weeks of age, as described in Table 2 below.

TABLE 2

Treatment Groups

| | |
|---|---|
| Control (Ctrl) | no treatment (n = 6) |

8 Weeks of Age

| | |
|---|---|
| 100 µg | 100 µg/mouse/injection on Day 0, Day 1, Day 4, Day 7 and Day 14 (n = 6) |
| 200 µg | 200 µg/mouse/injection on Day 0, Day 1, Day 4, Day 7 and Day 14 (n = 6) (Data not presented) |
| Multiple | 100 µg/mouse/injection three times per week for 5 weeks (n = 6). (Data not presented; Dosing was discontinued after blood spotted in urine at week 12) |

27 Weeks of Age

| | |
|---|---|
| 100 µg | 100 µg/mouse/injection on Day 0, Day 1, Day 4, Day 7 and Day 14 (n = 6) |
| 50 µg | 50 µg/mouse/injection on Day 0, Day 1, Day 4, Day 7 and Day 14 (n = 6) (Data not presented) |
| Multiple | 30 µg/mouse/injection three times per week for 3 weeks (n = 6). (Data not presented) |

The results of these experiments are shown in FIGS. 6-10.

Example 6

Figure 11:
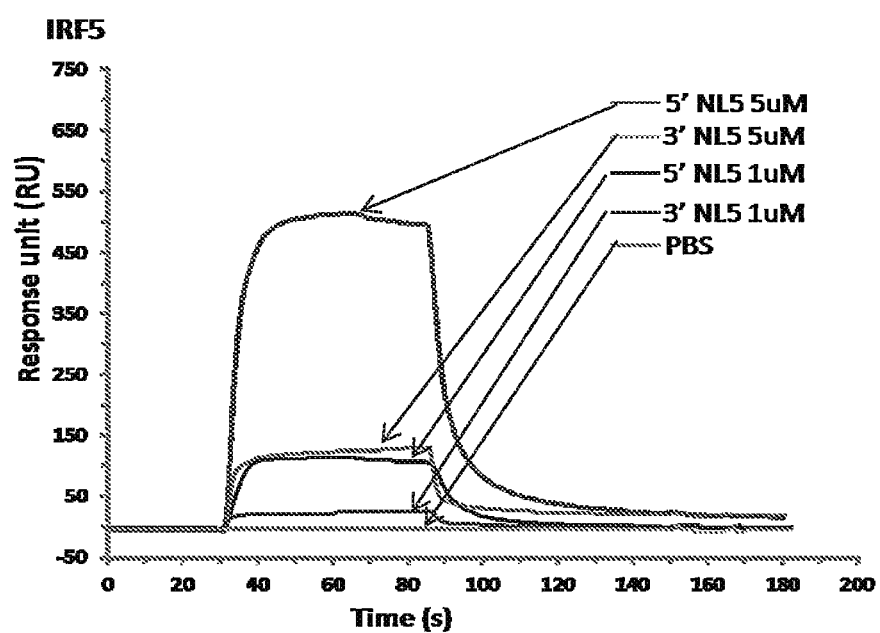
FIG. 11. Specific binding of the 5'-terminal inhibitor to human recombinant full-length IRF5. 20 µg/mL recombinant IRF5 was immobilized on the Biacore Sensor Chip CM5 at a flow rate of 10 µL/min using manual injection (450RU). Running buffer was filtered 1×PBS with 0.05% P20 run at a flow rate of 30 µl/min. Contact time—60 sec; Dissociation time—120 sec. Samples were run on a Biacore-T200.

The specific binding of the 5'-NLS inhibitor (DRQIKIWFQNRRMKWKKPRRVRLK (SEQ ID NO:3)) and the 3'-NLS inhibitor (DRQIKIWFQNRRMKWKKPREKKLI (SEQ ID NO:4)) (Life Tein, LLC) to human recombinant full-length IRF5 was investigated. Specifically, 20 µg/mL recombinant IRF5 was immobilized on the Biacore Sensor Chip CM5 at a flow rate of 10 µL/min using manual injection (450RU). Running buffer was filtered 1×PBS with 0.05% P20 run at a flow rate of 30 µl/min. Contact time—60 sec; Dissociation time—120 sec. Samples were run on a Biacore-T200. Specific binding of the 5'-NLS inhibitor to human recombinant full-length IRF5 is shown in FIG. 11.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A method of treating systemic lupus erythematosus (SLE) in a subject in need thereof comprising administering to the subject a therapeutically effective amount of a polypeptide comprising a cell penetrating peptide sequence and an amino-terminus interferon regulatory factor 5 (IRF5) nuclear localization signal (NLS) sequence,
wherein the cell penetrating peptide sequence is selected from the group consisting of DRQIKIWFQNRRMKWKK (SEQ ID NO:5), AAVALLPAVLLALLAP (SEQ ID NO:9), GRKKRRQRRRPPQ (SEQ ID NO:10), CSIPPEVKFNKPFVYLI (SEQ ID NO:11), KKWKMRRNQFWVKVQRG (SEQ ID NO:12), KLLKLLLKLWLKLLKLLL (SEQ ID NO: 13), INLKALAALAKKIL (SEQ ID NO:14), RQIKIWFQNRRMKWKKGG (SEQ ID NO: 15) and GWTLNSAGYLLGKINLKALAALAKKIL (SEQ ID NO:16); and
wherein the amino-terminus interferon regulatory factor 5 (IRF5) nuclear localization signal (NLS) sequence is PRRVRLK (SEQ ID NO:1).

2. The method of claim 1, wherein the polypeptide inhibits interferon regulatory factor 5 (IRF5).

3. The method of claim 1, wherein the polypeptide inhibits interferon regulatory factor 5 (IRF5) nuclear localization.

4. The method of claim 1, wherein the polypeptide binds to interferon regulatory factor 5 (IRF5).

5. The method of claim 1, wherein the polypeptide inhibits pathogenic autoantibody production in the subject.

6. The method of claim 1, wherein the polypeptide reduces proteinuria in the subject.

* * * * *